US008632556B2

(12) United States Patent
Jacobs et al.

(10) Patent No.: US 8,632,556 B2
(45) Date of Patent: Jan. 21, 2014

(54) METHODS AND DEVICES FOR CROSSING CHRONIC TOTAL OCCLUSIONS

(75) Inventors: Peter Alan Jacobs, Minneapolis, MN (US); Chad John Kugler, Buffalo, MN (US); Matthew Jonathan Olson, Crystal, MN (US); Ross Arlen Olson, Anoka, MN (US); David B. Robinson, Chanhassen, MN (US)

(73) Assignee: Bridgepoint Medical, Inc., Plymouth, MN (US)

( * ) Notice: Subject to any disclaimer, the term of this patent is extended or adjusted under 35 U.S.C. 154(b) by 723 days.

(21) Appl. No.: 12/289,154

(22) Filed: Oct. 21, 2008

(65) Prior Publication Data

US 2009/0124899 A1 May 14, 2009

Related U.S. Application Data

(60) Provisional application No. 60/999,879, filed on Oct. 22, 2007.

(51) Int. Cl.
*A61B 17/22* (2006.01)

(52) U.S. Cl.
USPC ........................................................ 606/159

(58) Field of Classification Search
USPC ......... 606/127, 128, 167, 180, 170, 185, 159; 604/7, 8, 508, 264, 104, 510, 95.01
See application file for complete search history.

(56) References Cited

U.S. PATENT DOCUMENTS

| | | | |
|---|---|---|---|
| 4,020,829 A * | 5/1977 | Willson et al. ................ 600/434 |
| 4,233,983 A | 11/1980 | Rocco | |
| 4,569,347 A | 2/1986 | Frisbie | |
| 4,581,017 A | 4/1986 | Sahota | |
| 4,621,636 A | 11/1986 | Fogarty | |
| 4,747,821 A | 5/1988 | Kensey et al. | |
| 4,762,130 A | 8/1988 | Fogarty et al. | |
| 4,774,949 A | 10/1988 | Fogarty | |
| 4,819,634 A | 4/1989 | Shiber | |
| 4,878,495 A | 11/1989 | Grayzel | |
| 4,976,689 A | 12/1990 | Buchbinder et al. | |

(Continued)

FOREIGN PATENT DOCUMENTS

| WO | WO 0178822 A2 | 10/2001 |
|---|---|---|
| WO | WO 2007/033052 A2 | 3/2007 |

(Continued)

OTHER PUBLICATIONS

International Preliminary Report On Patentability for PCT/US08/11976 issued on Jan. 13, 2009 (7 pages).

(Continued)

*Primary Examiner* — Ryan Severson
*Assistant Examiner* — Rachel S Papeika
(74) *Attorney, Agent, or Firm* — Seager, Tufte & Wickhem, LLC

(57) ABSTRACT

The present disclosure is directed to a method of facilitating treatment via a vascular wall defining a vascular lumen containing an occlusion therein. The method may include providing an intravascular device having a distal portion and a longitudinal axis and inserting the intravascular device into the vascular lumen. The method may further include positioning the distal portion in the vascular wall, rotating the intravascular device about the longitudinal axis, and advancing the intravascular device within the vascular wall.

47 Claims, 18 Drawing Sheets

(56) References Cited

U.S. PATENT DOCUMENTS

| | | | |
|---|---|---|---|
| 4,979,939 A | 12/1990 | Shiber | |
| 4,990,134 A | 2/1991 | Auth | |
| 5,071,406 A | 12/1991 | Jang | |
| 5,127,917 A | 7/1992 | Niederhauser et al. | |
| 5,161,534 A | 11/1992 | Berthiaume et al. | |
| 5,193,546 A | 3/1993 | Shaknovich | |
| 5,201,753 A | 4/1993 | Lampropoulos et al. | |
| 5,263,493 A | 11/1993 | Avitall | |
| 5,275,610 A | 1/1994 | Eberbach | |
| 5,324,263 A | 6/1994 | Kraus et al. | |
| 5,356,418 A | 10/1994 | Shturman | |
| 5,372,587 A | 12/1994 | Hammerslag et al. | |
| 5,383,856 A | 1/1995 | Bersin | |
| 5,385,152 A | 1/1995 | Abele et al. | |
| 5,409,453 A | 4/1995 | Lundquist et al. | |
| 5,415,637 A | 5/1995 | Khosravi | |
| 5,464,395 A | 11/1995 | Faxon et al. | |
| 5,501,667 A | 3/1996 | Verduin, Jr. | |
| 5,505,702 A | 4/1996 | Arney | |
| 5,534,007 A | 7/1996 | St Germain et al. | |
| 5,555,883 A | 9/1996 | Avitall | |
| 5,571,122 A | 11/1996 | Kelly et al. | |
| 5,571,169 A | 11/1996 | Plaia et al. | |
| 5,603,720 A | 2/1997 | Kieturakis | |
| 5,643,298 A | 7/1997 | Nordgren et al. | |
| 5,645,529 A | 7/1997 | Fagan et al. | |
| 5,655,548 A | 8/1997 | Nelson et al. | |
| 5,695,506 A | 12/1997 | Pike et al. | |
| 5,728,133 A | 3/1998 | Kontos | |
| 5,741,270 A | 4/1998 | Hansen et al. | |
| 5,741,429 A | 4/1998 | Donadio, III et al. | |
| 5,759,172 A | 6/1998 | Weber et al. | |
| 5,779,721 A | 7/1998 | Nash | |
| 5,807,241 A | 9/1998 | Heimberger | |
| 5,824,071 A | 10/1998 | Nelson et al. | |
| 5,830,222 A | 11/1998 | Makower | |
| 5,830,224 A | 11/1998 | Cohn et al. | |
| 5,843,050 A | 12/1998 | Jones et al. | |
| 5,882,329 A * | 3/1999 | Patterson et al. | 604/500 |
| 5,910,133 A | 6/1999 | Gould et al. | |
| 5,916,194 A | 6/1999 | Jacobsen et al. | |
| 5,935,108 A | 8/1999 | Katoh et al. | |
| 5,944,686 A | 8/1999 | Patterson et al. | |
| 5,954,713 A | 9/1999 | Newman et al. | |
| 5,957,900 A | 9/1999 | Ouchi | |
| 5,968,064 A | 10/1999 | Selmon et al. | |
| 5,989,276 A | 11/1999 | Houser et al. | |
| 6,010,449 A | 1/2000 | Selmon et al. | |
| 6,013,055 A | 1/2000 | Bampos et al. | |
| 6,015,405 A | 1/2000 | Schwartz et al. | |
| 6,022,343 A | 2/2000 | Johnson et al. | |
| 6,033,414 A | 3/2000 | Tockman et al. | |
| 6,036,707 A | 3/2000 | Spaulding | |
| 6,036,717 A | 3/2000 | Mers Kelly et al. | |
| 6,059,750 A | 5/2000 | Fogarty et al. | |
| 6,068,638 A | 5/2000 | Makower | |
| 6,071,281 A | 6/2000 | Burnside et al. | |
| 6,071,292 A | 6/2000 | Makower et al. | |
| 6,081,738 A | 6/2000 | Hinohara et al. | |
| 6,099,542 A | 8/2000 | Cohn et al. | |
| 6,120,516 A | 9/2000 | Selmon et al. | |
| 6,126,649 A | 10/2000 | VanTassel et al. | |
| 6,155,264 A | 12/2000 | Ressemann et al. | |
| 6,157,852 A | 12/2000 | Selmon et al. | |
| 6,159,225 A | 12/2000 | Makower | |
| 6,183,432 B1 | 2/2001 | Milo | |
| 6,186,972 B1 | 2/2001 | Nelson et al. | |
| 6,190,353 B1 | 2/2001 | Makower et al. | |
| 6,203,559 B1 | 3/2001 | Davis et al. | |
| 6,217,527 B1 | 4/2001 | Selmon et al. | |
| 6,217,549 B1 | 4/2001 | Selmon et al. | |
| 6,221,049 B1 | 4/2001 | Selmon et al. | |
| 6,231,546 B1 | 5/2001 | Milo et al. | |
| 6,231,587 B1 | 5/2001 | Makower | |
| 6,235,000 B1 | 5/2001 | Milo et al. | |
| 6,241,667 B1 | 6/2001 | Vetter et al. | |
| 6,246,914 B1 | 6/2001 | de la Rama et al. | |
| 6,254,588 B1 | 7/2001 | Jones et al. | |
| 6,258,052 B1 | 7/2001 | Milo | |
| 6,266,550 B1 | 7/2001 | Selmon et al. | |
| 6,277,133 B1 | 8/2001 | Kanesaka | |
| 6,283,940 B1 | 9/2001 | Mulholland | |
| 6,283,951 B1 | 9/2001 | Flaherty et al. | |
| 6,283,983 B1 | 9/2001 | Makower et al. | |
| 6,287,317 B1 | 9/2001 | Makower et al. | |
| 6,302,875 B1 | 10/2001 | Makower et al. | |
| 6,330,884 B1 | 12/2001 | Kim | |
| 6,337,142 B2 | 1/2002 | Harder et al. | |
| 6,358,244 B1 | 3/2002 | Newman et al. | |
| 6,375,615 B1 | 4/2002 | Flaherty et al. | |
| 6,379,319 B1 * | 4/2002 | Garibotto et al. | 600/585 |
| 6,387,119 B2 | 5/2002 | Wolf et al. | |
| 6,398,798 B2 | 6/2002 | Selmon et al. | |
| 6,416,523 B1 | 7/2002 | Lafontaine | |
| 6,428,552 B1 | 8/2002 | Sparks | |
| 6,432,127 B1 | 8/2002 | Kim et al. | |
| 6,447,539 B1 | 9/2002 | Nelson et al. | |
| 6,475,226 B1 | 11/2002 | Belef et al. | |
| 6,482,216 B1 * | 11/2002 | Hiblar et al. | 606/159 |
| 6,485,458 B1 | 11/2002 | Takahashi | |
| 6,491,660 B2 | 12/2002 | Guo et al. | |
| 6,491,707 B2 | 12/2002 | Makower et al. | |
| 6,506,178 B1 | 1/2003 | Schubart et al. | |
| 6,508,824 B1 | 1/2003 | Flaherty et al. | |
| 6,508,825 B1 | 1/2003 | Selmon et al. | |
| 6,511,458 B2 | 1/2003 | Milo et al. | |
| 6,514,217 B1 | 2/2003 | Selmon et al. | |
| 6,544,230 B1 | 4/2003 | Flaherty et al. | |
| 6,561,998 B1 | 5/2003 | Roth et al. | |
| 6,565,583 B1 | 5/2003 | Deaton et al. | |
| 6,569,143 B2 | 5/2003 | Alchas et al. | |
| 6,569,145 B1 | 5/2003 | Shmulewitz et al. | |
| 6,569,150 B2 | 5/2003 | Teague et al. | |
| 6,579,311 B1 | 6/2003 | Makower | |
| 6,589,164 B1 | 7/2003 | Flaherty | |
| 6,599,304 B1 | 7/2003 | Selmon et al. | |
| 6,602,241 B2 | 8/2003 | Makower et al. | |
| 6,613,081 B2 | 9/2003 | Kim et al. | |
| 6,616,675 B1 | 9/2003 | Evard et al. | |
| 6,623,448 B2 | 9/2003 | Slater | |
| 6,638,247 B1 | 10/2003 | Selmon et al. | |
| 6,638,293 B1 | 10/2003 | Makower et al. | |
| 6,655,386 B1 | 12/2003 | Makower et al. | |
| 6,656,195 B2 | 12/2003 | Peters et al. | |
| 6,660,024 B1 | 12/2003 | Flaherty et al. | |
| 6,669,709 B1 | 12/2003 | Cohn et al. | |
| 6,685,648 B2 | 2/2004 | Flaherty et al. | |
| 6,685,716 B1 | 2/2004 | Flaherty et al. | |
| 6,694,983 B2 | 2/2004 | Wolf et al. | |
| 6,709,444 B1 | 3/2004 | Makower | |
| 6,719,725 B2 | 4/2004 | Milo et al. | |
| 6,726,677 B1 | 4/2004 | Flaherty et al. | |
| 6,746,426 B1 | 6/2004 | Flaherty et al. | |
| 6,746,462 B1 | 6/2004 | Selmon et al. | |
| 6,746,464 B1 | 6/2004 | Makower | |
| 6,786,884 B1 | 9/2004 | DeCant, Jr. et al. | |
| 6,800,085 B2 | 10/2004 | Selmon et al. | |
| 6,824,550 B1 | 11/2004 | Noriega et al. | |
| 6,830,577 B2 | 12/2004 | Nash et al. | |
| 6,837,868 B1 | 1/2005 | Fajnztajn | |
| 6,860,892 B1 | 3/2005 | Tanaka et al. | |
| 6,863,684 B2 | 3/2005 | Kim et al. | |
| 6,866,676 B2 | 3/2005 | Kieturakis et al. | |
| 6,884,225 B2 | 4/2005 | Kato et al. | |
| 6,905,505 B2 | 6/2005 | Nash et al. | |
| 6,929,009 B2 | 8/2005 | Makower et al. | |
| 6,936,056 B2 | 8/2005 | Nash et al. | |
| 6,942,641 B2 | 9/2005 | Seddon | |
| 6,949,125 B2 | 9/2005 | Robertson | |
| 6,991,617 B2 | 1/2006 | Hektner et al. | |
| 7,004,173 B2 | 2/2006 | Sparks et al. | |
| 7,025,758 B2 | 4/2006 | Klint | |
| 7,056,325 B1 | 6/2006 | Makower et al. | |
| 7,059,330 B1 | 6/2006 | Makower et al. | |

(56) References Cited

U.S. PATENT DOCUMENTS

| | | | |
|---|---|---|---|
| 7,083,588 | B1 | 8/2006 | Shmulewitz et al. |
| 7,094,230 | B2 | 8/2006 | Flaherty et al. |
| 7,105,031 | B2 | 9/2006 | Letort |
| 7,134,438 | B2 | 11/2006 | Makower et al. |
| 7,137,990 | B2 | 11/2006 | Hebert et al. |
| 7,159,592 | B1 | 1/2007 | Makower et al. |
| 7,179,270 | B2 | 2/2007 | Makower |
| 7,191,015 | B2 | 3/2007 | Lamson et al. |
| 7,229,421 | B2 | 6/2007 | Jen et al. |
| 7,316,655 | B2 | 1/2008 | Garibotto et al. |
| 7,377,910 | B2 | 5/2008 | Katoh et al. |
| 7,465,286 | B2 | 12/2008 | Patterson et al. |
| 7,485,107 | B2 | 2/2009 | DiFiore et al. |
| 2001/0000041 | A1* | 3/2001 | Selmon et al. ............ 600/585 |
| 2001/0056273 | A1 | 12/2001 | Ewers |
| 2002/0029052 | A1 | 3/2002 | Evans et al. |
| 2002/0052637 | A1 | 5/2002 | Houser et al. |
| 2002/0103459 | A1 | 8/2002 | Sparks et al. |
| 2003/0028200 | A1 | 2/2003 | Berg et al. |
| 2003/0040737 | A1 | 2/2003 | Merril et al. |
| 2003/0109809 | A1 | 6/2003 | Jen et al. |
| 2003/0120195 | A1 | 6/2003 | Milo et al. |
| 2003/0167038 | A1 | 9/2003 | Yozu et al. |
| 2003/0236542 | A1* | 12/2003 | Makower .................. 606/167 |
| 2004/0015193 | A1 | 1/2004 | Lamson et al. |
| 2004/0059280 | A1 | 3/2004 | Makower et al. |
| 2004/0102719 | A1 | 5/2004 | Keith et al. |
| 2004/0133225 | A1 | 7/2004 | Makower |
| 2004/0158143 | A1 | 8/2004 | Flaherty et al. |
| 2004/0167554 | A1 | 8/2004 | Simpson et al. |
| 2004/0230156 | A1 | 11/2004 | Schreck et al. |
| 2004/0249277 | A1 | 12/2004 | Kato et al. |
| 2004/0249338 | A1 | 12/2004 | DeCant, Jr. et al. |
| 2005/0038467 | A1 | 2/2005 | Hebert et al. |
| 2005/0049574 | A1 | 3/2005 | Petrick et al. |
| 2005/0171478 | A1 | 8/2005 | Selmon et al. |
| 2005/0177105 | A1 | 8/2005 | Shalev |
| 2005/0216044 | A1 | 9/2005 | Hong |
| 2005/0261663 | A1 | 11/2005 | Patterson et al. |
| 2006/0094930 | A1 | 5/2006 | Sparks et al. |
| 2006/0135984 | A1 | 6/2006 | Kramer et al. |
| 2006/0229646 | A1* | 10/2006 | Sparks ..................... 606/159 |
| 2006/0271078 | A1 | 11/2006 | Modesitt |
| 2007/0083220 | A1 | 4/2007 | Shamay |
| 2007/0088230 | A1 | 4/2007 | Terashi et al. |
| 2007/0093779 | A1 | 4/2007 | Kugler et al. |
| 2007/0093780 | A1 | 4/2007 | Kugler et al. |
| 2007/0093781 | A1 | 4/2007 | Kugler et al. |
| 2007/0093782 | A1 | 4/2007 | Kugler et al. |
| 2007/0093783 | A1 | 4/2007 | Kugler et al. |
| 2007/0265596 | A1 | 11/2007 | Jen et al. |
| 2008/0103443 | A1 | 5/2008 | Kabrick et al. |
| 2008/0228171 | A1 | 9/2008 | Kugler et al. |
| 2008/0243065 | A1 | 10/2008 | Rottenberg et al. |
| 2008/0243067 | A1 | 10/2008 | Rottenberg et al. |
| 2009/0088685 | A1 | 4/2009 | Kugler et al. |
| 2009/0209910 | A1 | 8/2009 | Kugler et al. |
| 2009/0270890 | A1 | 10/2009 | Robinson et al. |
| 2010/0063534 | A1 | 3/2010 | Kugler et al. |
| 2010/0069945 | A1 | 3/2010 | Olson et al. |

FOREIGN PATENT DOCUMENTS

| | | |
|---|---|---|
| WO | WO 2007/082216 A1 | 7/2007 |
| WO | WO 2008/063621 A2 | 5/2008 |
| WO | WO 2008/116600 A1 | 10/2008 |
| WO | WO 2009/054943 A1 | 4/2009 |
| WO | WO 2009/100129 A2 | 8/2009 |
| WO | WO 2009/134346 A2 | 11/2009 |
| WO | WO 2010/019241 A1 | 2/2010 |
| WO | WO 2010/044816 A1 | 4/2010 |

OTHER PUBLICATIONS

International Search Report for PCT/US08/11976 issued on Jan. 13, 2009 (1 page).

Colombo, Antonio et al., *Treating Chronic Total Occlusions Using Subintimal Tracking and Reentry: The STAR Technique*, Catheterization and Cardiovascular Interventions, vol. 64:407-411 (2005).

English translation of claims granted in European Application No. 08734691.2 (European national phase of WO 2008/116600 A1), dated Feb. 3, 2012 (3 pages).

Extended European Search Report for European Application No. 08841515.3, dated Mar. 30, 2012 (6 pages).

* cited by examiner

METHODS AND DEVICES FOR CROSSING CHRONIC TOTAL OCCLUSIONS

CROSS-REFERENCE TO RELATED APPLICATION

This application claims the benefit of U.S. Provisional Application No. 60/999,879, filed Oct. 22, 2007, which is herein incorporated by reference in its entirety.

FIELD OF THE INVENTION

The inventions described herein relate to devices and associated methods for the treatment of chronic total occlusions. More particularly, the inventions described herein relate to devices and methods for crossing chronic total occlusions and establishing a pathway blood flow past the chronic total occlusions.

BACKGROUND OF THE INVENTION

Due to age, high cholesterol and other contributing factors, a large percentage of the population has arterial atherosclerosis that totally occludes portions of the patient's vasculature and presents significant risks to patient health. For example, in the case of a total occlusion of a coronary artery, the result may be painful angina, loss of cardiac tissue or patient death. In another example, complete occlusion of the femoral and/or popliteal arteries in the leg may result in limb threatening ischemia and limb amputation.

Commonly known endovascular devices and techniques are either inefficient (time consuming procedure), have a high risk of perforating a vessel (poor safety) or fail to cross the occlusion (poor efficacy). Physicians currently have difficulty visualizing the native vessel lumen, can not accurately direct endovascular devices toward the visualized lumen, or fail to advance devices through the lesion. Bypass surgery is often the preferred treatment for patients with chronic total occlusions, but less invasive techniques would be preferred.

Described herein are devices and methods employed to exploit the vascular wall of a vascular lumen for the purpose of bypassing a total occlusion of an artery. Exploitation of a vascular wall may involve the passage of an endovascular device into and out of said wall which is commonly and interchangeable described as false lumen access, intramural access, submedial access or in the case of this disclosure, subintimal access.

BRIEF SUMMARY

Described herein are devices and methods employed to exploit the vascular wall of a vascular lumen for the purpose of bypassing a total occlusion of an artery. Exploitation of a vascular wall may involve the passage of an endovascular device into and out of said wall which is commonly and interchangeable described as false lumen access, intramural access, submedial access or in the case of this disclosure, subintimal access.

In one aspect, the present disclosure is directed to a method of facilitating treatment via a vascular wall defining a vascular lumen containing an occlusion therein. The method may include providing an intravascular device having a distal portion and a longitudinal axis and inserting the intravascular device into the vascular lumen. The method may further include positioning the distal portion in the vascular wall, rotating the intravascular device about the longitudinal axis, and advancing the intravascular device within the vascular wall.

In another aspect, the present disclosure is direct to a device for facilitating treatment via a vascular wall defining a vascular lumen containing an occlusion therein. The device may include a shaft having a distal end and a proximal end. The shaft may include a coil having a plurality of filars wound in a helical shape, the coil extending from the distal end of the shaft to the proximal end of the shaft, and a sleeve, having a proximal end and a distal end, the sleeve extending from the distal end of the shaft and covering a portion of the coil. The device may further include a tip fixed to the distal end of the shaft, and a hub fixed to the proximal end of the shaft.

DETAILED DESCRIPTION OF EXEMPLARY EMBODIMENTS

The following detailed description should be read with reference to the drawings in which similar elements in different drawings are numbered the same. The drawings, which are not necessarily to scale, depict illustrative embodiments and are not intended to limit the scope of the invention.

Figure 1:
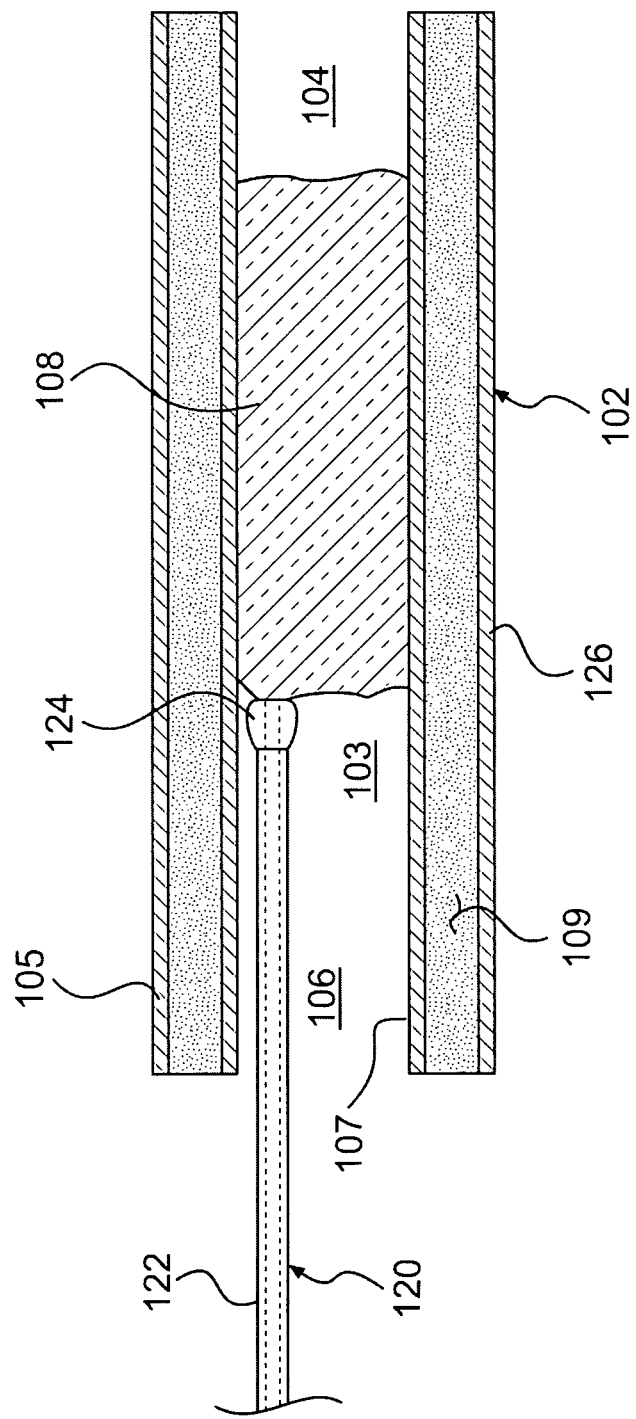
FIG. 1 is a cross-sectional view of an artery.

FIG. 1 is a cross-sectional view of an artery 102 having a wall 126. In FIG. 1, wall 126 of artery 102 is shown having three layers. The outermost layer of wall 126 is the adventitia 105 and the innermost layer of wall 126 is the intima 107. The tissues extending between intima 107 and adventitia 105 may be collectively referred to as the media 109. For purposes of illustration, intima 107, media 109 and adventitia 105 are each shown as a single homogenous layer in FIG. 1. In the human body, however, the intima and the media each comprise a number of sub-layers. The transition between the external most portion of the intima and the internal most portion of the media is sometimes referred to as the subintimal space.

Intima 107 defines a true lumen 106 of artery 102. In FIG. 1, an occlusion 108 is shown blocking true lumen 106. Occlusion 108 divides true lumen 106 into a proximal segment 103 and a distal segment 104. A crossing device 120 is disposed in proximal segment 103 of true lumen 106. Crossing device 120 may be used to establish a channel between proximal segment 103 and distal segment 104. Crossing device 120 of FIG. 1 comprises a tip 124 that is fixed to a distal end of a shaft 122.

Figure 2:
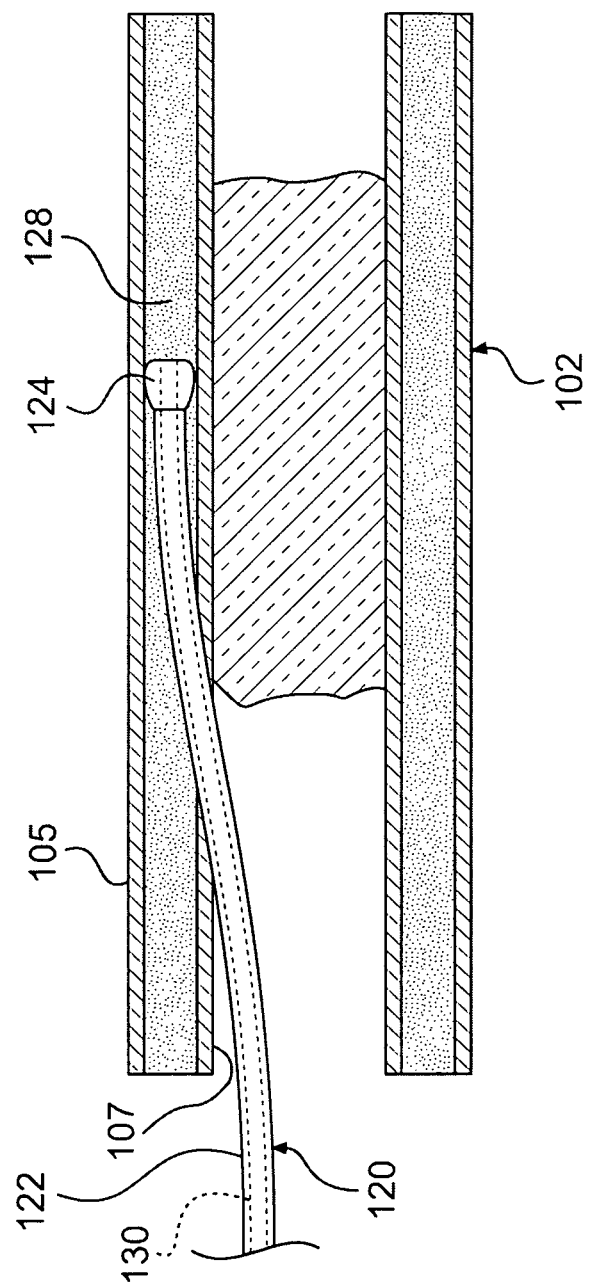
FIG. 2 is an additional view of the artery shown in the previous figure.

FIG. 2 is an additional view of artery 102 shown in the previous figure. In the embodiment of FIG. 2, the distal end of crossing device 120 has been advanced in a distal direction so that tip 124 is disposed in subintimal space 128. With reference to FIG. 2, it will be appreciated that tip 124 has passed through intima 107 and is disposed between intima 107 and adventitia 105 of artery 102. The embodiment of FIG. 2 and other embodiments described herewithin show access to the subintimal space 128 by way of example, not limitation, as the crossing device 120 may alternatively pass through the occlusion 108 thus remaining disposed in the true lumen 106.

In the embodiment of FIG. 2, shaft 122 of crossing device 120 defines a lumen 130. Lumen 130 may be used to deliver fluids into the body. For example, radiopaque fluid may be injected through lumen 130 and into subintimal space 128. In some useful embodiments, lumen 130 is dimensioned to receive a guidewire.

Figure 3:
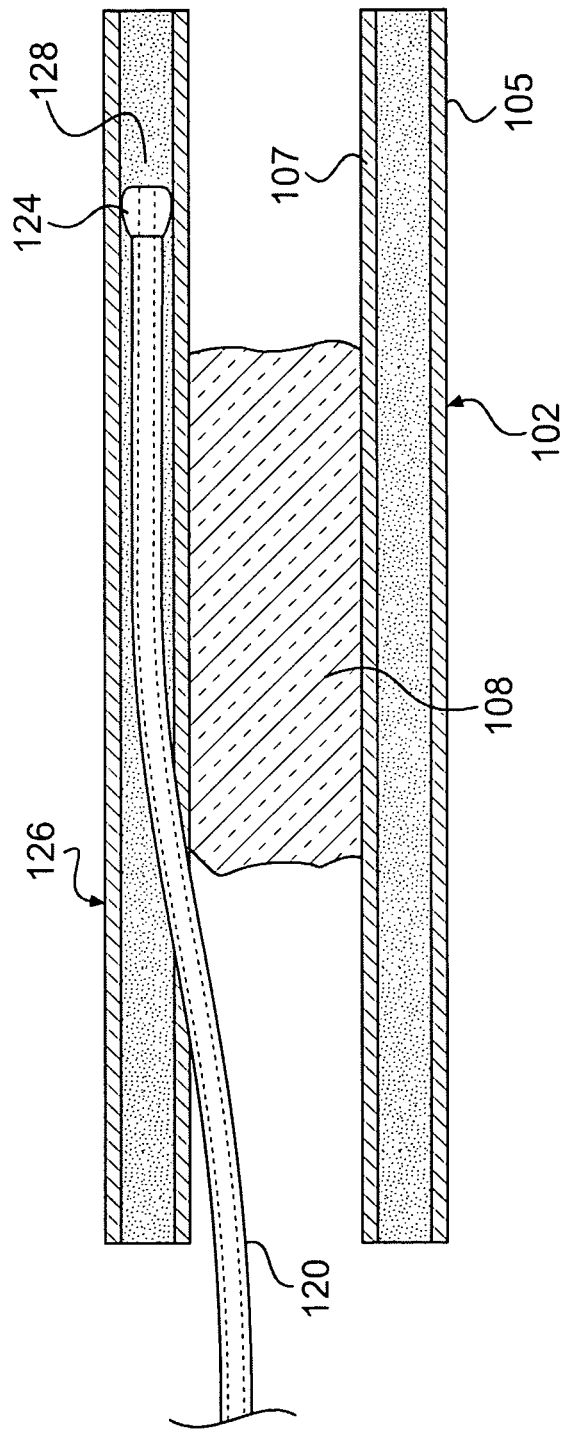
FIG. 3 is an additional view of the artery shown in the previous figure.

FIG. 3 is an additional view of artery 102 shown in the previous figure. In the embodiment of FIG. 3, the distal end of crossing device 120 has been advanced so that tip 124 has moved in an axial direction through subintimal space 128. With reference to FIG. 3, it will be appreciated that tip 124 has moved distally past occlusion 108. In FIG. 3, tip 124 is shown residing between intima 107 and adventitia 105 of artery 102. Axial advancement of tip 124 may cause blunt dissection of the layers forming wall 126 of artery 102. Alternatively, the tip may cause blunt dissection of the materials comprising the occlusion 108 (not shown).

In some useful methods in accordance with the present disclosure, crossing device 120 is rotated about it's longitudinal axis and moved in a direction parallel to it's longitudinal axis simultaneously. When this is the case, rotation of crossing device 120 may reduce resistance to the axial advancement of crossing device 120. These methods take advantage of the fact that the kinetic coefficient of friction is usually less than the static coefficient of friction for a given frictional interface. Rotating crossing device 120 assures that the coefficient of friction at the interface between the crossing device and the surround tissue will be a kinetic coefficient of friction and not a static coefficient of friction.

Figure 4:
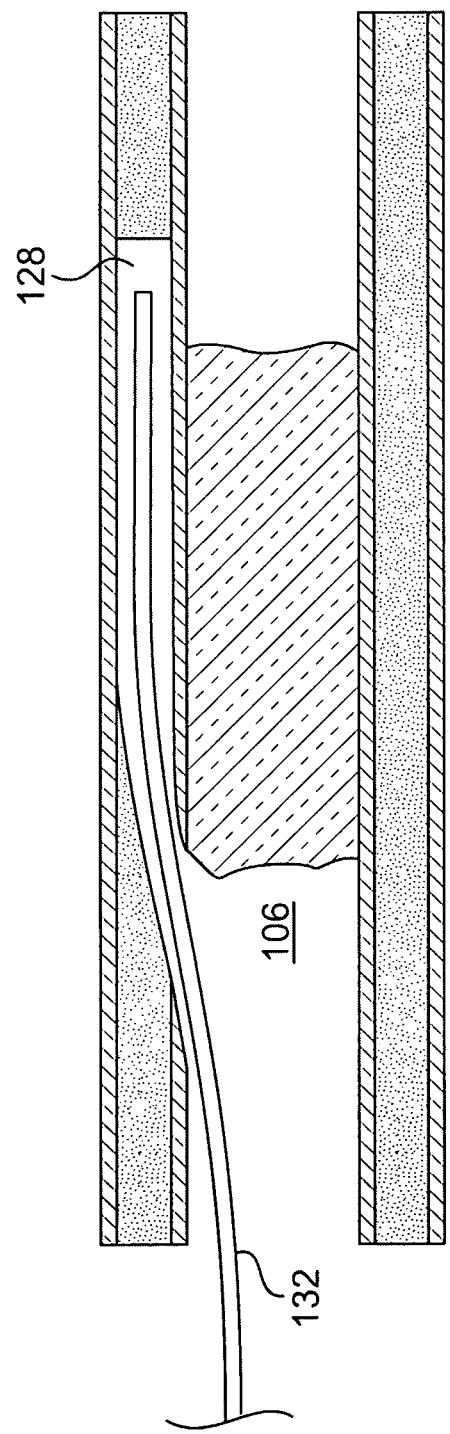
FIG. 4 is an additional view of the artery shown in the previous figure.

FIG. 4 is an additional view of artery 102 shown in the previous figure. In the embodiment of FIG. 4, crossing device 120 has been withdrawn from true lumen 106 of artery 102. With reference to FIG. 4, it will be appreciated that a guidewire 132 remains in the position formerly occupied by crossing device 120.

The position of guidewire 132 shown in FIG. 4 may be achieved using crossing device 120. Guidewire 132 may be positioned, for example, by first placing crossing device 120 in the position shown in the previous figure, then advancing guidewire 132 through lumen 130 defined by shaft 122 of crossing device 120. Alternately, guidewire 132 may be disposed within lumen 130 while crossing device 120 is advanced through the vasculature of a patient. When this is the case, guidewire 132 may be used to aid in the process of steering crossing device 120 through the vasculature.

With guidewire 132 in the position shown in FIG. 4, guidewire 132 may be used to direct other devices to subintimal space 128. For example, a catheter may be advanced over guidewire 132 until the distal end of the catheter is disposed in subintimal space 128. After reaching the subintimal space, the catheter may be used to dilate subintimal space 128. Examples of catheters that may be used to dilate the subintimal space include balloon catheters and atherectomy catheters.

Figure 5:
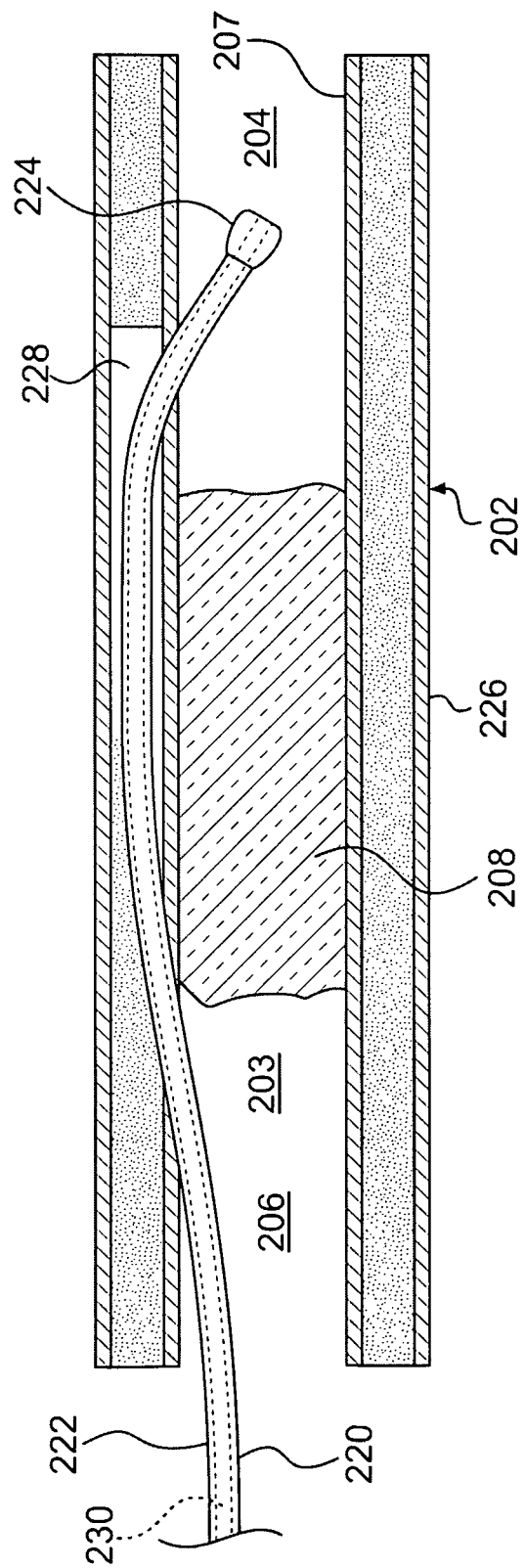
FIG. 5 is a cross-sectional view of an artery.

FIG. 5 is a cross sectional view of an artery 202 having a wall 226. In FIG. 5, a crossing device 220 is shown extending through subintimal space 228 and around an occlusion 208. In FIG. 5, occlusion 208 is shown blocking a true lumen 206 defined by an intima 207 of wall 226. Occlusion 208 divides true lumen 206 into a proximal segment 203 and a distal segment 204. When a crossing member in accordance with some embodiments of the present disclosure is advanced through the subintimal space of an artery, the distal end of the crossing device may penetrate the intima and enter the distal segment of the true lumen after advancing beyond an occlusion.

In the embodiment of FIG. 5, a tip 224 of crossing device 220 is disposed in distal segment 204. Accordingly, it will be appreciated that crossing device 220 has pierced intima 207 distally of occlusion 208 and entered distal segment 204 of artery 202. In FIG. 5, shaft 222 is shown extending through intima 207 and subintimal space 228. Shaft 222 of crossing device 220 may define a lumen 230.

Figure 6:
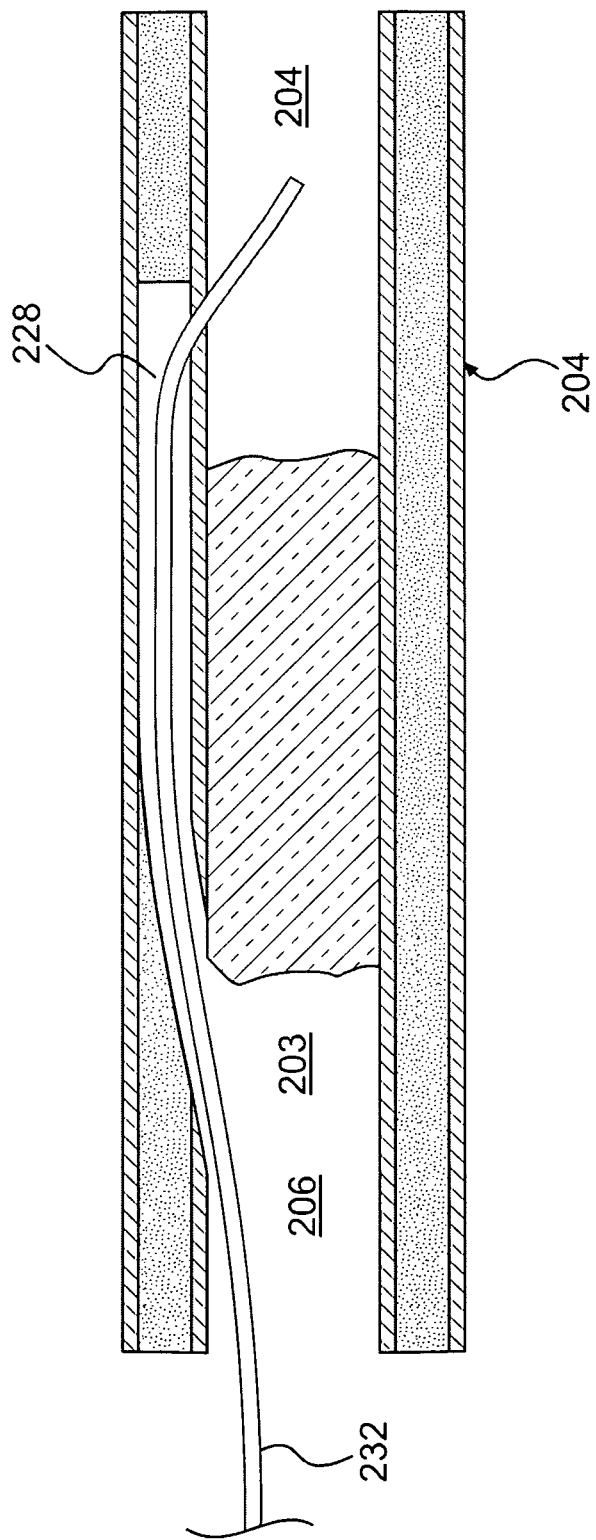
FIG. 6 is an additional view of the artery shown in the previous figure.

FIG. 6 is an additional view of artery 202 shown in the previous figure. In the embodiment of FIG. 6, crossing device 220 has been withdrawn leaving a guidewire 232 in the position shown in FIG. 6.

The position of guidewire 232 shown in FIG. 6 may be achieved using crossing device 220. Guidewire 232 may be positioned, for example, by first placing crossing device 220 in the position shown in the previous figure, then advancing guidewire 232 through lumen 230 defined by shaft 222 of crossing device 220. Alternately, guidewire 232 may be disposed within lumen 230 while crossing device 220 is advanced through the vasculature of a patient. When this is the case, guidewire 232 may be used to aid in the process of steering crossing device 220 through the vasculature of a patient.

Devices such as balloon angioplasty catheters and atherectomy catheters may be advanced over guidewire 232 and into subintimal space 228. In this way, these devices may be used in conjunction with guidewire 232 to establish a blood flow path between proximal segment 203 of true lumen 206 and distal segment 204 of true lumen 206. This path allows blood to flow through subintimal space 228 and around occlusion 208.

Figure 7:
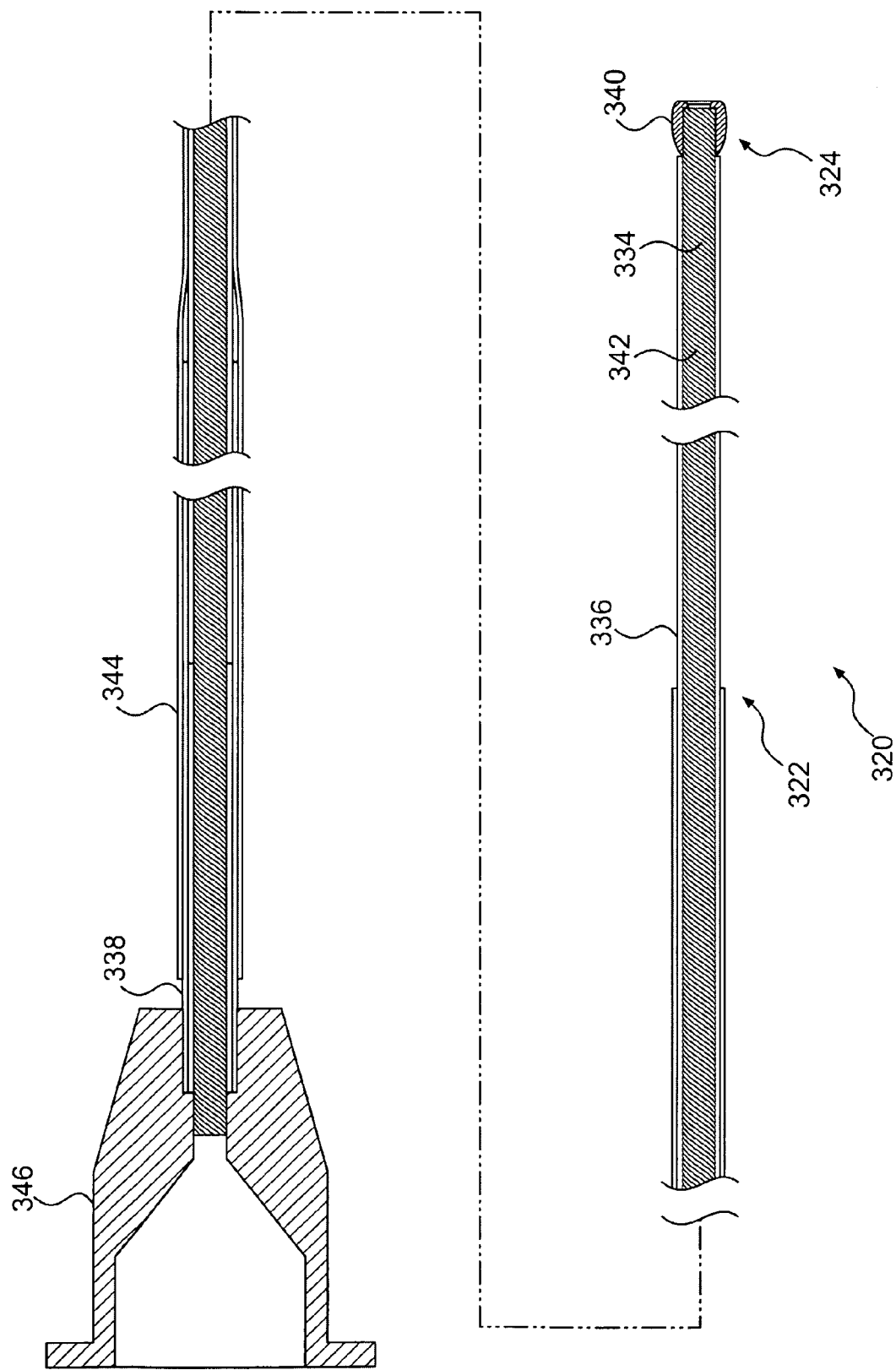
FIG. 7 is a partial cross-sectional view of an exemplary crossing device.

FIG. 7 is a partial cross-sectional view of an exemplary crossing device 320. Crossing device 320 of FIG. 7 comprises a tip 324 that is fixed to a distal end of a shaft 322. In the exemplary embodiment of FIG. 7, shaft 322 comprises a coil 334, a sleeve 336, a tubular body 338, and a sheath 344.

Tip 324 is fixed to a distal portion of coil 334. Coil 334 comprises a plurality of filars 342 that are wound in a generally helical shape. In some useful embodiments of crossing device 320, coil 334 comprises eight, nine or ten filars wound into the shape illustrated in FIG. 7. Crossing device 320 includes a sleeve 336 that is disposed about a portion of coil 334. Sleeve 336 may comprise, for example, PET shrink tubing, i.e. polyethylene terephthalate.

Sleeve 336 and coil 334 both extend into a lumen defined by a tubular body 338. Tubular body 338 may comprise, for example hypodermic tubing formed of Nitinol, i.e. nickel titanium. With reference to FIG. 7, it will be appreciated that a proximal portion of sleeve 336 is disposed between tubular body 338 and coil 334. In some embodiments of crossing device 320, a distal portion of tubular body 338 defines a helical cut. This helical cut may be formed, for example, using a laser cutting process. The helical cut may be shaped and dimensioned to provide an advantageous transition in lateral stiffness proximate the distal end of tubular body 338.

A proximal portion of coil 334 extends proximally beyond the distal end of tubular body 338. A hub 346 is fixed to a proximal portion of coil 334 and a proximal portion of tubular body 338. Hub 346 may comprise, for example, a luer fitting. Sheath 344 is disposed about a portion of tubular body 338 and a portion of sleeve 336. In some embodiments of crossing device 320, sheath 344 comprises HYTREL, a thermoplastic elastomer.

With reference to FIG. 7, it will be appreciated that tubular body 338, coil 334, sleeve 336, and sheath 344 each have a proximal end and a distal end. The proximal end of sheath 344 is disposed between the proximal end of tubular body 338 and the proximal end of sleeve 336. The distal end of sleeve 336 is positioned proximate tip 324 that is fixed to the distal end of coil 334. The distal end of sheath 344 is located between the distal end of tubular body 338 and the distal end of sleeve 336. With reference to FIG. 7, it will be appreciated that sheath 344 overlays the distal end of tubular body 338.

With reference to FIG. 7, it will be appreciate that tip 324 has a generally rounded shape. The generally rounded shape of tip 324 may reduce the likelihood that crossing device 320 will penetrate the adventitia of an artery. Tip 324 may be formed from a suitable metallic material including but not limited to stainless steel, silver solder, and braze. Tip 324 may also be formed from suitable polymeric materials or adhesives including but not limited to polycarbonate, polyethylene and epoxy. In some embodiments of crossing device 320, outer surface 340 of tip 324 comprises a generally non-abrasive surface. For example, outer surface 340 may have a surface roughness of 25 micrometers or less. A tip member having a relatively smooth outer surface may reduce the likelihood that the tip member will abrade the adventitia of an artery.

Figure 8:
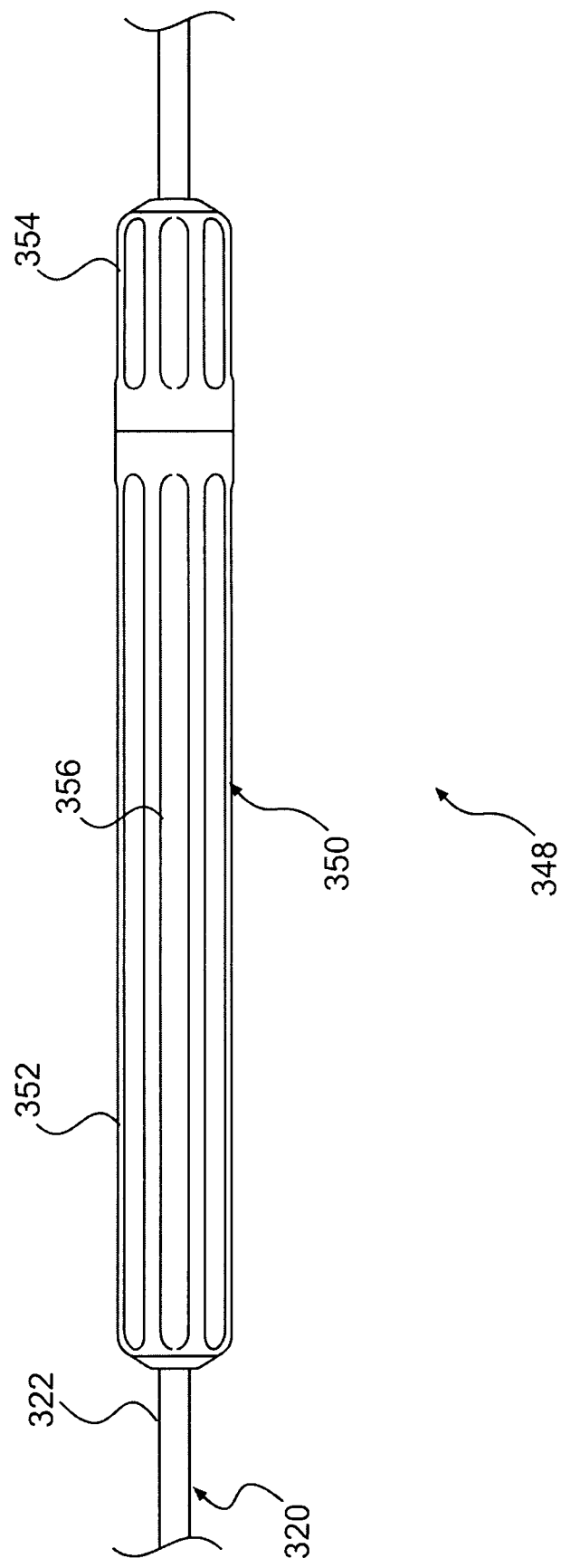
FIG. 8 is a plan view showing an assembly including the crossing device shown in the previous figure.

FIG. 8 is a plan view showing an assembly 348 including crossing device 320 shown in the previous figure. In the embodiment of FIG. 8, a handle assembly 350 is coupled to crossing device 320. In FIG. 8, handle assembly 350 is shown disposed about a proximal portion of shaft 322 of crossing device 320. Handle assembly 350 comprises a handle body 352 and a handle cap 354.

In some useful embodiments in accordance with the present disclosure, handle assembly 350 is long enough to receive the thumb and for fingers of a physician's right and left hands. When this is the case, a physician can use two hands to rotate handle assembly 350. In the embodiment of FIG. 8, grooves 356 are formed in handle body 352 and handle cap 354. Grooves 356 may improve the physician's ability to grip handle assembly 350.

Figure 9:
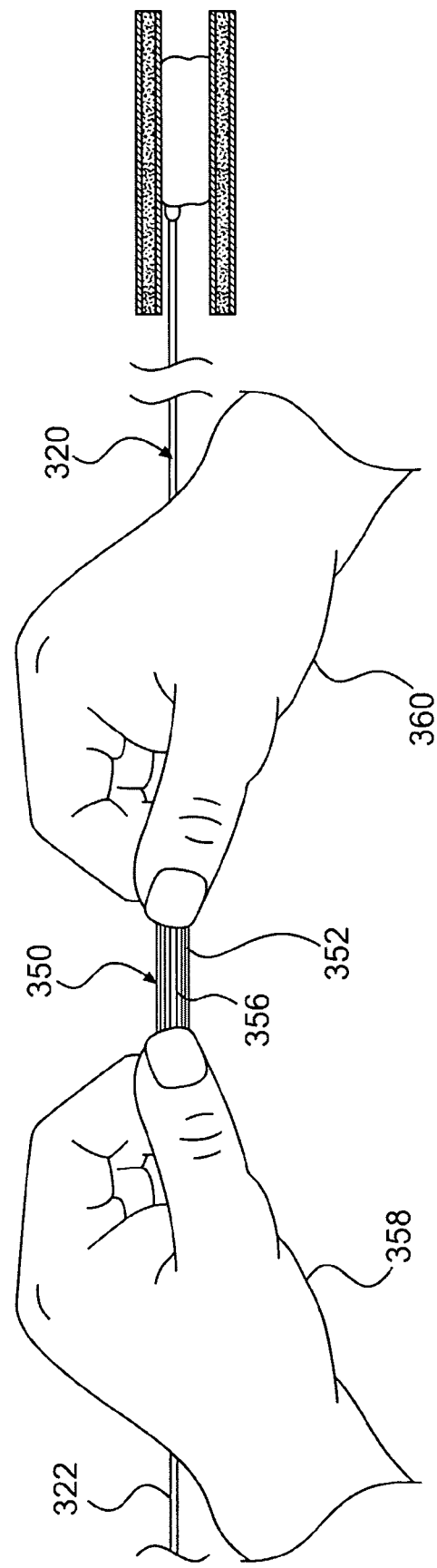
FIG. 9 is a plan view of the assembly shown in the previous figure.

FIG. 9 is an additional plan view showing assembly 348 shown in the previous figure. In FIG. 9, a proximal portion of handle assembly 350 is positioned between the thumb and forefinger of a left hand 358. A distal portion of handle assembly 350 is disposed between the thumb and forefinger of a right hand 360.

In some useful methods, crossing device 320 is rotated and axially advanced simultaneously. Rotation of crossing device 320 can be achieved by rolling handle assembly 350 between the thumb and forefinger one hand. Two hands can also be used as shown in FIG. 9. Rotating crossing device 320 assures that the coefficient of friction at the interface between the crossing device and the surround tissue will be a kinetic coefficient of friction and not a static coefficient of friction.

In some useful methods in accordance with the present disclosure, crossing device 320 is rotated at a rotational speed of 2 to 200 revolutions per minute. In some particularly useful methods in accordance with the present disclosure, crossing device 320 is rotated at a rotational speed of 50 and 150 revolutions per minute. Crossing device 320 may be rotated by hand as depicted in FIG. 9. It is also contemplated that a mechanical device (e.g., an electric motor) may be used to rotate crossing device 320.

Figure 10:
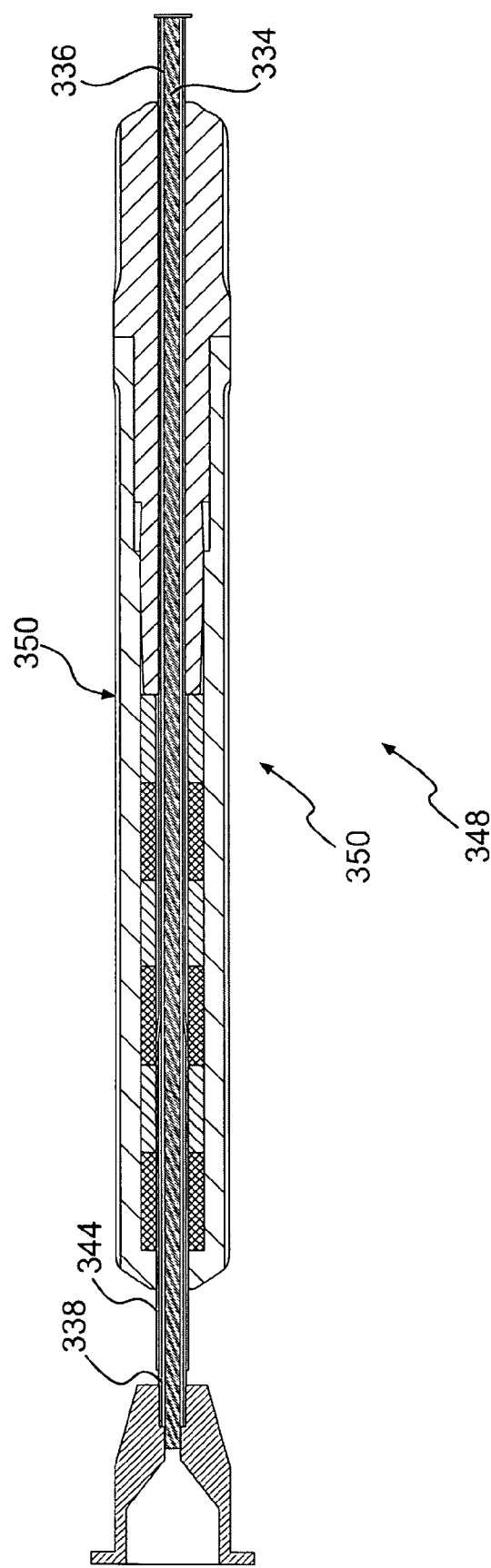
FIG. 10 is a cross-sectional view of the assembly shown in the previous figure.

FIG. 10 is a cross-sectional view of assembly 348 shown in the previous figure. With reference to FIG. 10 it will be appreciated that handle assembly 350 is disposed about sheath 344, tubular body 338, sleeve 336 and coil 334.

Figure 11:
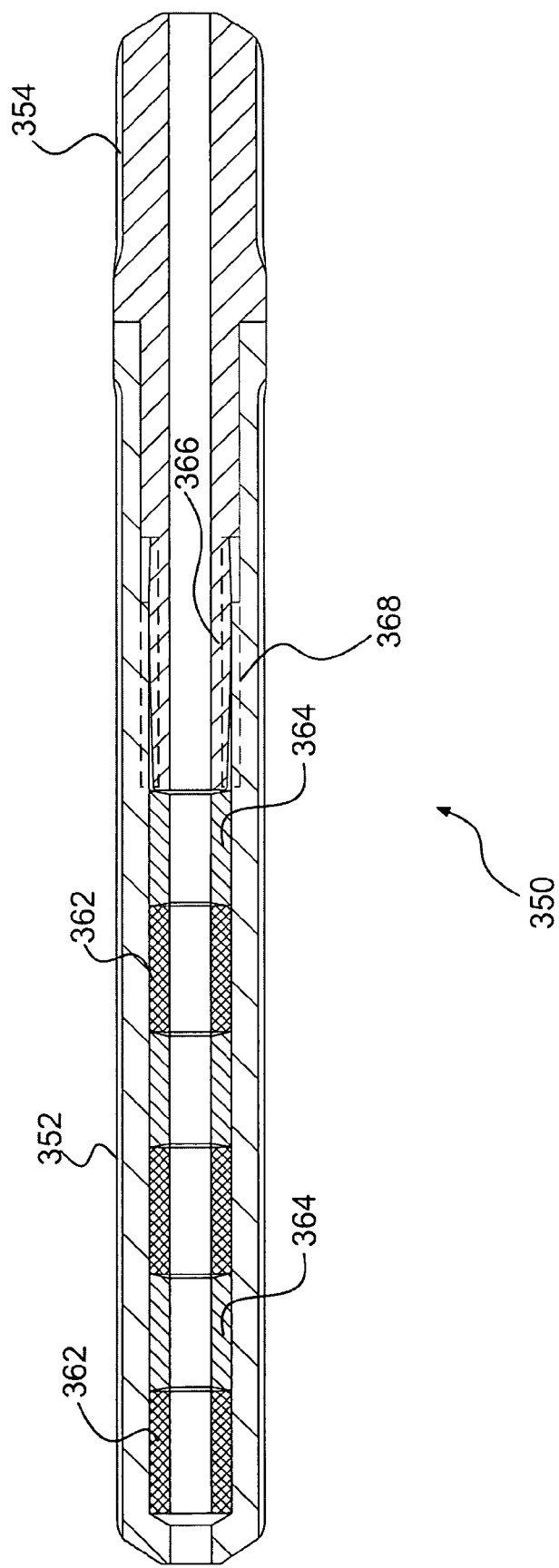
FIG. 11 is a cross sectional view of the handle assembly shown in the previous figure.

FIG. 11 is a cross sectional view of handle assembly 350 shown in the previous figure. With reference to FIG. 11, it will be appreciated that handle assembly 350 includes a plurality of grip sleeves 362 and a plurality of spacers 364. In the embodiment of FIG. 11, handle cap 354 includes male threads 366 that engage female threads 368 in handle body 352.

When handle cap 354 is rotated relative to handle body 352, the threads produce relative longitudinal motion between handle cap 354 and handle body 352. In other words, handle cap 354 can be screwed into handle body 352. As handle cap 354 is advanced into handle body 352, the inner end of handle cap 354 applies a compressive force to grip sleeves 362. Grip sleeves 362 are made from an elastomeric material. The compression forces applied to grip sleeves 362 by handle body 352 and handle cap 354 cause grip sleeves 362 to bulge. The bulging of grip sleeves 362 causes grip sleeves 362 to grip shaft 322 of crossing device 320.

The force that each grip sleeve 362 applies to the shaft is generally equally distributed about the circumference of the shaft. When this is the case, the likelihood that the shaft will be crushed by the grip sleeves is reduced. At the same time, the grip sleeves provide an interface that allows significant torque to be applied to the shaft when the handle is rotated.

Figure 12:
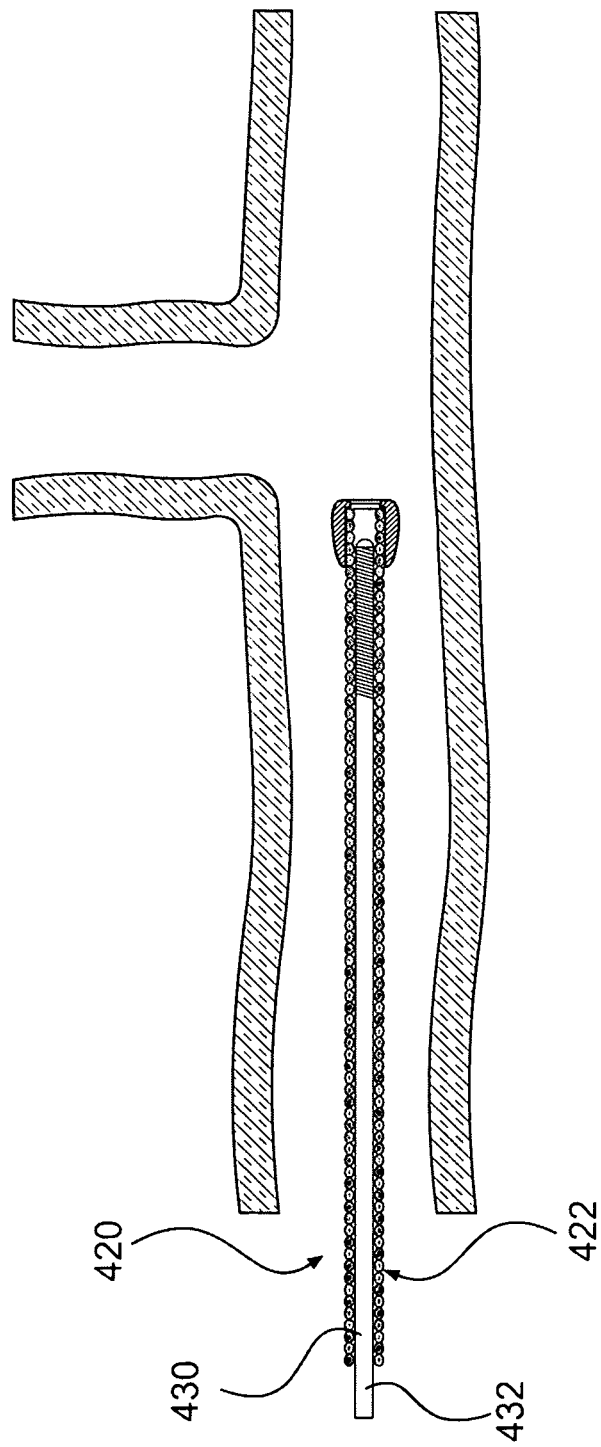
FIG. 12 is a partial cross-sectional view showing a guidewire that is disposed in a lumen defined by a shaft of a crossing device.
Figure 13:
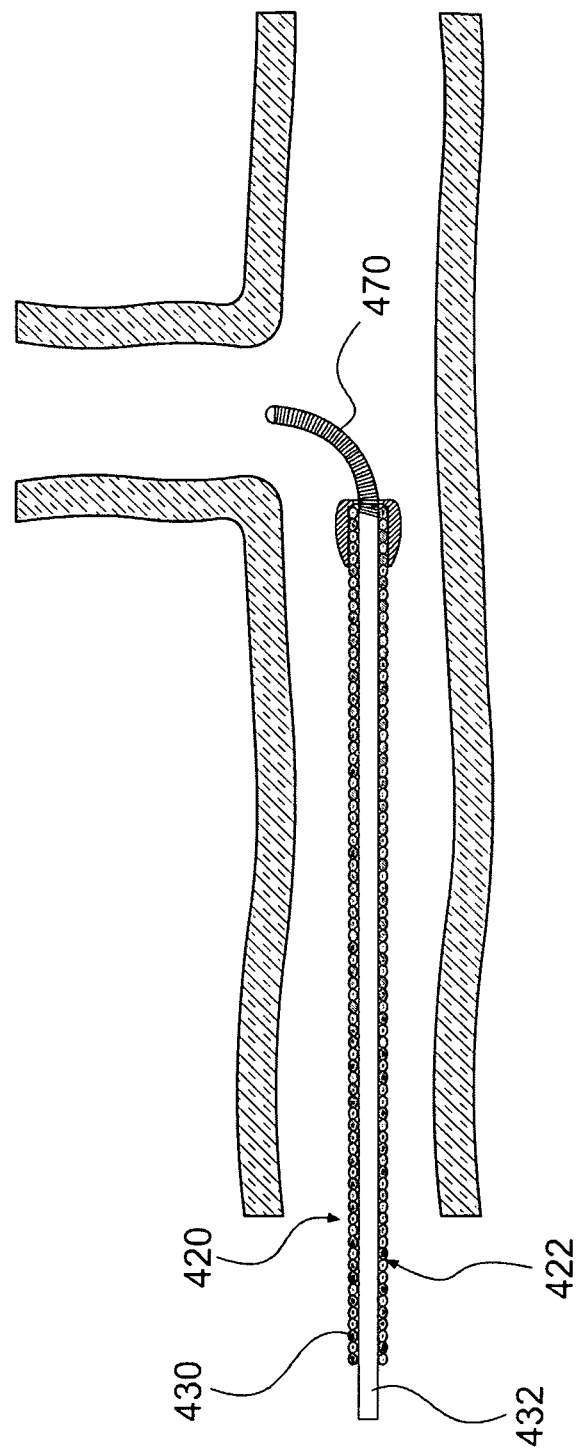
FIG. 13 is an additional view of the guidewire and crossing device shown in the previous figure.

FIG. 12 is a partial cross-sectional view showing a guidewire 432 that is disposed in a lumen 430 defined by a shaft 422 of a crossing device 420. FIG. 13 is an additional view showing guidewire 432 and crossing device 420 shown in FIG. 12. In some embodiments of crossing device 420, shaft 422 defines a lumen 430. When this is the case, a guidewire may be inserted into the lumen. The guidewire may be used to steer the crossing device. The guidewire may remain inside the lumen until it is needed for steering. When steering is needed, the guidewire may be advanced so that a portion of the guidewire extends beyond the distal end of the crossing device. A distal portion of the guidewire may then be advanced in the direction that the physician wishes to advance crossing device 420.

In the embodiment of FIG. 13, guidewire 432 has been distally advanced (relative to the position shown in FIG. 12). With reference to FIG. 13, it will be appreciated that a distal portion 470 of guidewire 432 is extending beyond the distal end of crossing device 420. In the embodiment of FIG. 13, distal portion 470 of guidewire 432 is biased to assume a generally curved shape when it is unrestrained by crossing device 420.

In the embodiment of FIG. 13, there are at least two degrees of freedom between guidewire 432 and crossing device 420. First, guidewire 432 and crossing device 420 are free to rotate relative to one another. Second, guidewire 432 and crossing device 420 are free to move in a longitudinal direction relative to one another. It is sometimes desirable to use guidewire 432 as an aid in directing crossing device 420 through the vasculature of a patient. When this is the case, distal portion 470 of guidewire 432 may be advanced beyond the distal end of crossing device 420. Guidewire 432 may then be rotated until distal portion 470 of guidewire 432 assumes a desired orientation.

Figure 14:
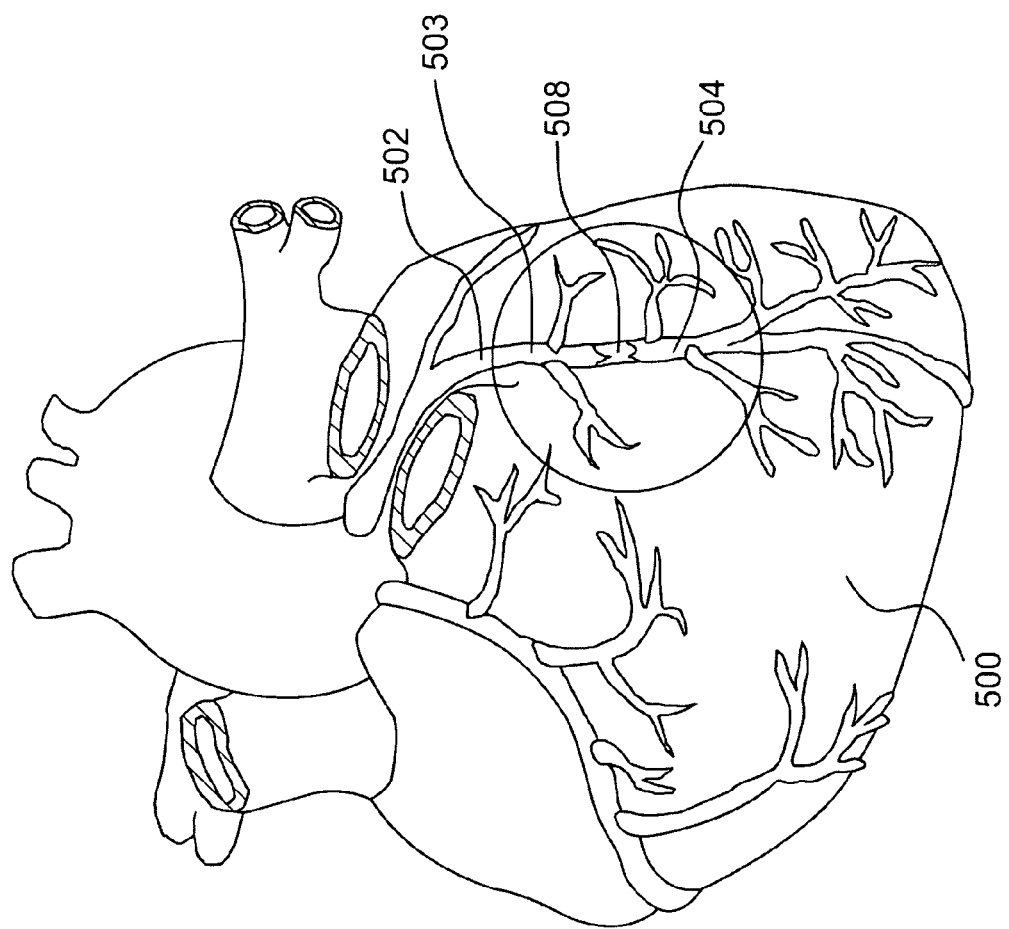
FIG. 14 is a plan view showing a heart including a coronary artery.

FIG. 14 shows a heart 500 including a coronary artery 502. An occlusion 508 is disposed in coronary artery 502. Occlusion 508 divides a lumen of coronary artery 502 into a proximal segment 503 and a distal segment 504. The proximal segment 503 may be easily accessed using endovascular devices and has adequate blood flow to supply the cardiac muscle. The distal segment 504 is not easily accessed with interventional devices and has significantly reduced blood flow as compared to proximal segment 503.

Figure 15B:
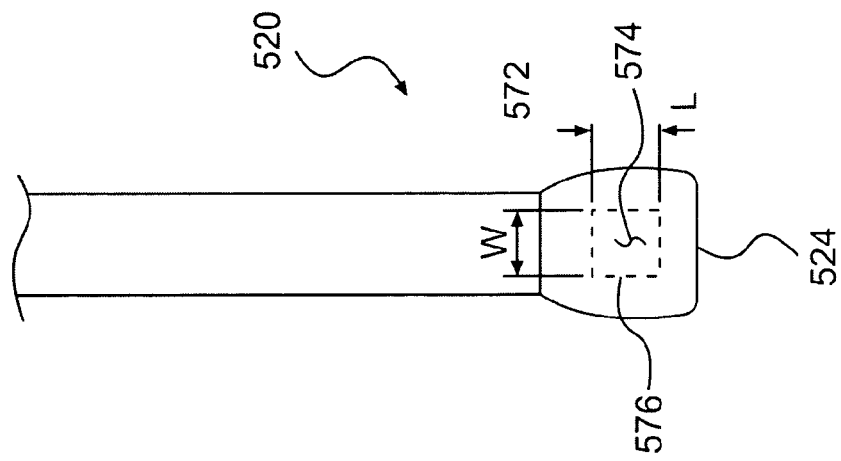
FIG. 15B is an enlarged plan view of a crossing device shown in FIG. 15A.
Figure 15A:
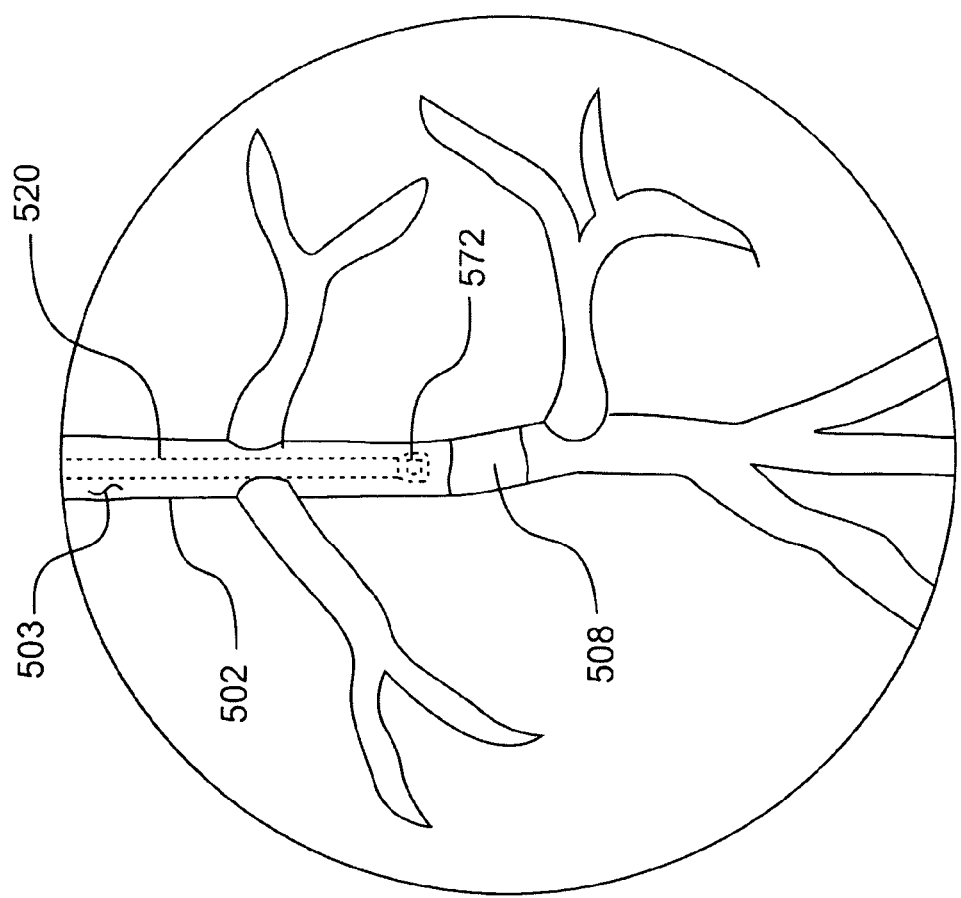
FIG. 15A is an enlarged view showing a portion of the heart shown in the previous figure.

FIG. 15A is an enlarged view showing a portion of heart 500 shown in the previous figure. In FIG. 15A, a crossing device 520 is disposed in proximal segment 503 of coronary artery 502. FIG. 15B is an enlarged plan view of crossing device 520 shown in FIG. 15A. Crossing device 520 comprises a tip 524 and a shaft 522.

Figure 16B:
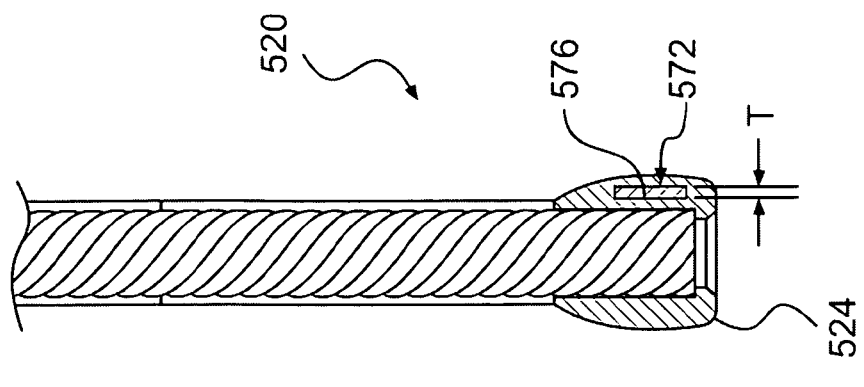
FIG. 16B is an enlarged plan view of a crossing device shown in FIG. 16A.
Figure 16A:
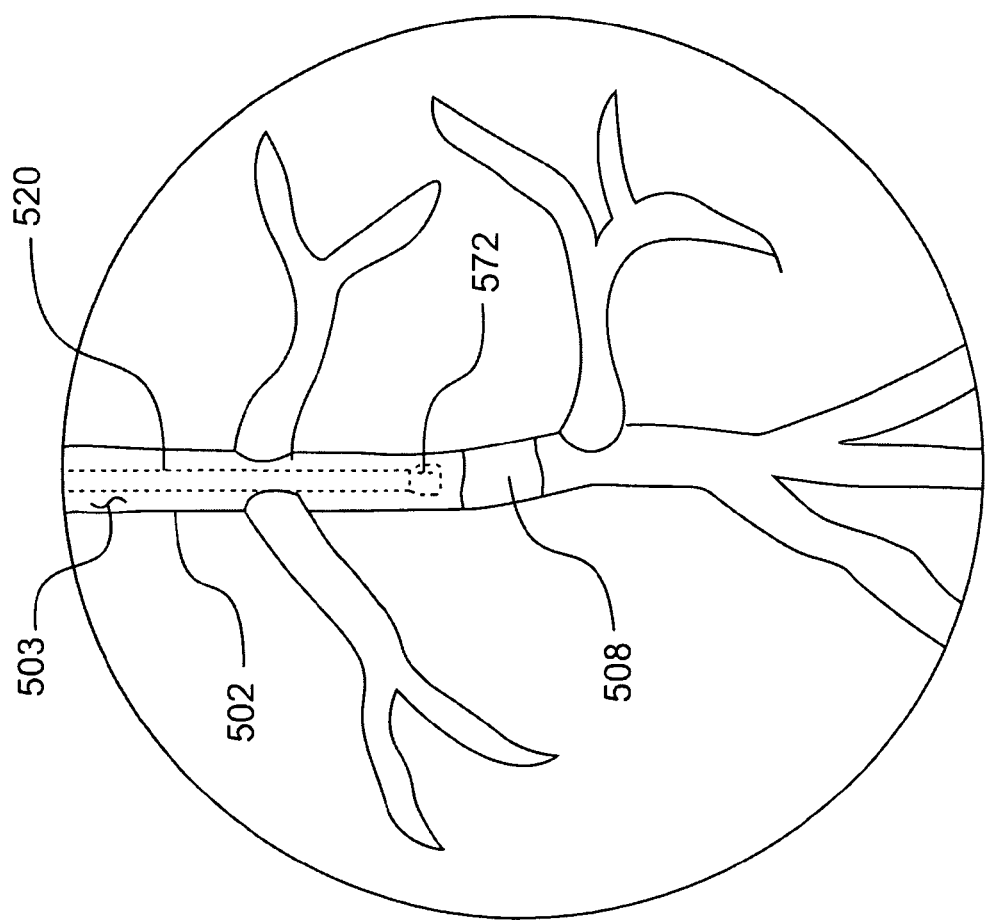
FIG. 16A is an additional view showing a crossing device disposed in a heart.

FIG. 16A is an additional view showing crossing device 520 disposed in heart 500. FIG. 16B is an enlarged plan view of crossing device 520 shown in FIG. 16A. In FIGS. 16A and 16B crossing device 520 has been rotated approximately ninety degrees relative to the position shown in FIGS. 15A and 15B.

Some useful methods in accordance with the present disclosure include the step of rotating crossing device 520. When the proximal portion of a crossing device is rotated, it may be desirable to confirm that the distal end of the crossing device is also rotating.

Many physicians have experience using guidewires. These physicians are aware that twisting the proximal end of a guidewire when the distal end of the guidewire is fixed may cause the guidewire to break due to twisting. Accordingly, many physicians may be hesitant to rotate an intravascular device more than a few revolutions unless they are certain that the distal end of the device is free to rotate.

One method for determining whether the tip of a crossing member is rotating may be described with reference to FIGS. 15A, 15B, 16A and 16B. As shown in the figures, crossing member 520 comprises a tip 524 fixed to the distal end of a shaft 522. Tip 524 comprises a radiopaque marker 572. Radiopaque marker 572 has a face 574 and an edge 576. Face 574 has a width W and a length L. Edge 576 has a length L and a thickness T. In some useful embodiments of crossing device 520, thickness T of radiopaque marker 572 is smaller then both length L and width W. When this is the case, radiopaque marker 572 may be used to provide a physician with visual feedback indicating that tip 524 of crossing device 520 is rotating.

During rotation of crossing device 520, the shape of radiopaque marker provides visual feedback assuring the physician that the tip of the crossing member is rotating as the physician rotates the proximal portion of the crossing member. Radiopaque marker 572 provides two different appearances while it is being rotated and observed using fluoroscopic methods. When edge 576 of radiopaque marker is viewed on a fluoroscopic display a first appearance is achieved. When face 574 of radiopaque marker 572 is viewed, it provides a second appearance on the fluoroscopic display. With reference to the figures, it will be appreciate that the first appearance has a smaller footprint than the second appearance. When the appearance of radiopaque marker 572 is alternating between the first appearance and the second appearance, the physician can infer that tip 524 is rotating. This visual feedback allows the physician to confirm that the distal end of crossing member is rotating.

Figure 17B:
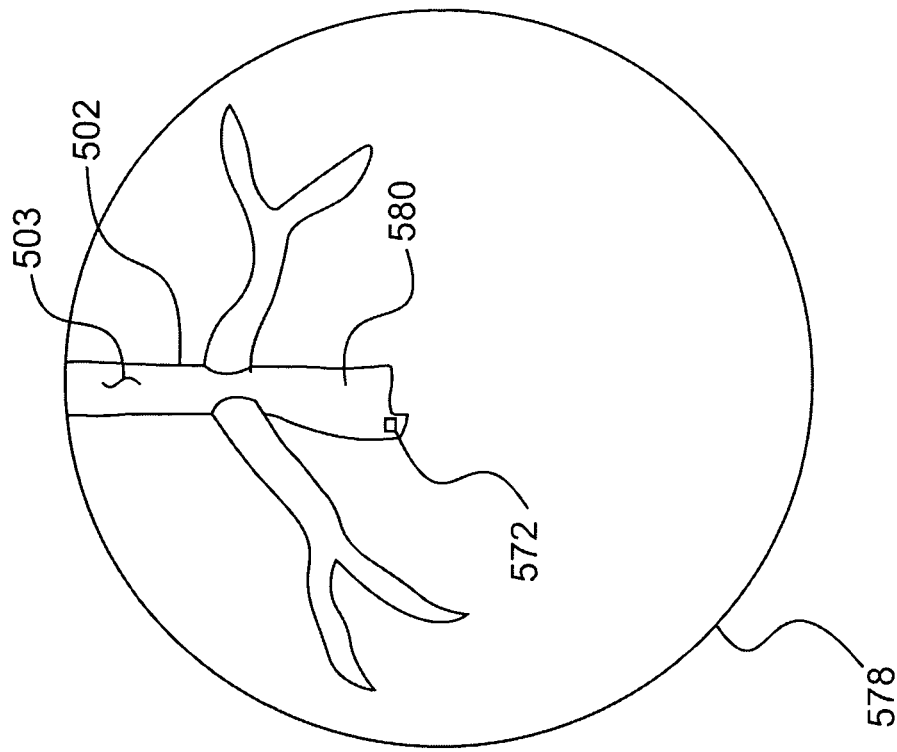
FIG. 17B is a representation of a fluoroscopic display produced when radiopaque fluid has been injected into the body from the distal end of a crossing device while the distal end of the crossing device is disposed in the true lumen of a coronary artery.
Figure 17A:
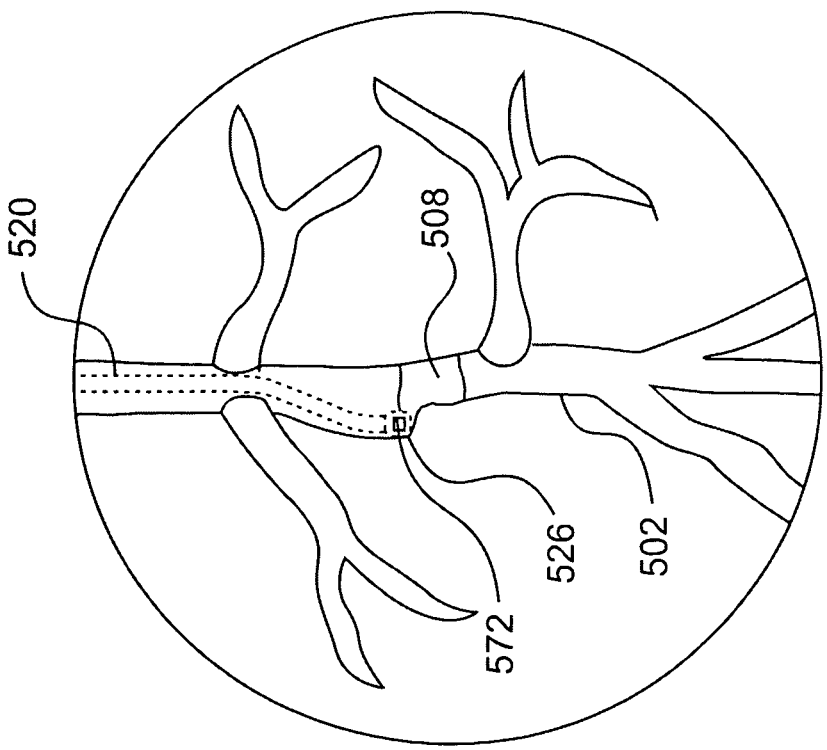
FIG. 17A is an enlarged view showing a portion of a heart and a crossing device that is extending into a proximal segment of a coronary artery of the heart.
Figure 18B:
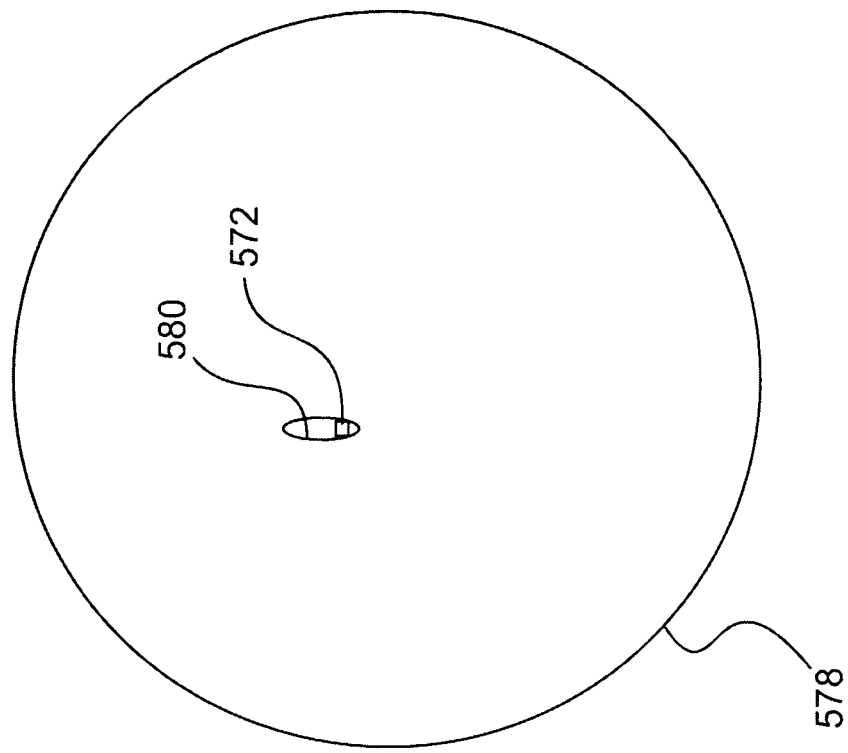
FIG. 18B is a representation of a fluoroscopic display produced when radiopaque fluid has been injected into the body from the distal end of a crossing device while the distal end of the crossing device is disposed in the subintimal space of a coronary artery.
Figure 18A:
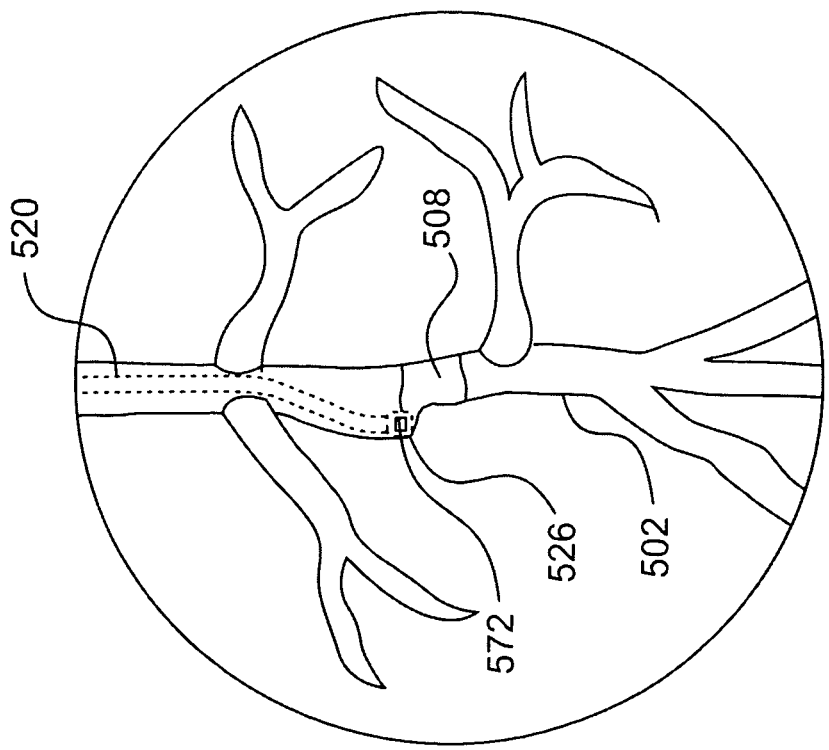
FIG. 18A is an enlarged view showing a portion of a heart and a crossing device that is extending into a proximal segment of a coronary artery of the heart.

FIGS. 17A and 18A each show a crossing device 520 comprising a tip 524 fixed to a shaft 522. Tip 524 comprises a radiopaque marker 572. Tip 524 of crossing device 520 has been advanced through a proximal segment 503 of a coronary artery 502. With reference to FIGS. 17A and 18A, it will be appreciated that tip 524 is near wall 526 of coronary artery 502 and an occlusion 508 that is located in the true lumen of coronary artery 502. When a surgical procedure is viewed on a fluoroscope, it may be difficult for the physician to determine whether or not tip 524 is disposed in the subintimal space of coronary artery 502. Methods for determining whether the tip is disposed in the subintimal space may be described with reference to FIGS. 17 and 18.

For example, one method in accordance with the present disclosure may include the steps of positioning the distal end of a crossing device in a position that may or may not be in the subintimal space of an artery and injecting radiopaque fluid into the body from the distal end of crossing device 520. If the radiopaque fluid remains in a localized area (e.g., in the subintimal space) then a physician viewing the radiopaque fluid on a fluoroscopic display can infer that the distal end of the crossing device is disposed in the subintimal space. If the radiopaque fluid rapidly enters the bloodstream and is carried through the vasculature, then the physician can infer that the distal end of the crossing device is disposed in the true lumen of the artery.

FIG. 17B is a representation of a fluoroscopic display 578 produced when radiopaque fluid has been injected into the body from the distal end of crossing device 520 while tip 524 is disposed in the true lumen of coronary artery 502. In FIG. 17B, the radiopaque fluid 580 has rapidly entered the bloodstream and has cause the vasculature in fluid communication with proximal segment 503 to become illuminated on fluoroscopic display 578. Radiopaque marker 572 is also visible in fluoroscopic display 578.

FIG. 18B is a representation of a fluoroscopic display 578 produced when radiopaque fluid has been injected into the body from the distal end of crossing device 520 while tip 524 is disposed in the subintimal space of coronary artery 502. In FIG. 18B, the radiopaque fluid 580 is disposed in a localized area (i.e., in the subintimal space). Radiopaque marker 572 is also visible in fluoroscopic display 578.

Additional methods are also contemplated. For example, negative pressure (i.e., sub atmospheric pressure) may be applied to the lumen defined by crossing device 520. The physician may observe the results of this application of negative pressure. If a partial vacuum is produced and little or no blood is drawn through the lumen, then the physician can infer that the distal end of the lumen is located in the subintimal space. If, on the other hand, blood is drawn through the lumen of the crossing member, then the physician can infer that the distal end of the crossing member is disposed in the true lumen of a blood vessel.

What is claimed is:

1. A method of treating a blood vessel with an intravascular device, the blood vessel having a vascular wall defining a vascular lumen containing an occlusion therein, the occlusion being disposed between a proximal segment of the vascular lumen and a distal segment of the vascular lumen, the method comprising:
    inserting the intravascular device into the vascular lumen, the intravascular device including a shaft defining a longitudinal axis and a tip located at a distal end of the shaft, wherein an outer diameter of the tip is greater than a diameter of the distal end of the shaft, a proximal portion of the tip tapering towards the shaft, and wherein the intravascular device defines a device lumen;
    rotating the intravascular device about the longitudinal axis to produce relative motion at an interface between the tip and surrounding tissue;
    advancing the tip out of the proximal segment of the vascular lumen into the vascular wall;
    advancing the intravascular device within the vascular wall to establish a channel in the vascular wall extending longitudinally across the occlusion;
    advancing the tip of the intravascular device into the distal segment of the vascular lumen distal of the occlusion;
    positioning a guidewire through the device lumen and into the vascular lumen beyond the occlusion; and
    withdrawing the intravascular device over the guidewire.

2. The method of claim 1, wherein the intravascular device is rotated at least a plurality of revolutions at a rotational speed between about 2 revolutions per minute and about 200 revolutions per minute.

3. The method of claim 2, wherein the intravascular device is rotated at a rotational speed between about 50 revolutions per minute and about 150 revolutions per minute.

4. The method of claim 1, further including stopping rotating and advancing the intravascular device when the tip of the intravascular device is advanced beyond the occlusion in the vascular lumen.

5. The method of claim 1, wherein rotating and advancing the intravascular device occur simultaneously.

6. The method of claim 1, wherein rotating the intravascular device includes rotating the entire intravascular device.

7. The method of claim 1, wherein rotating the intravascular device includes manually rotating a handle assembly positioned about the intravascular device.

8. The method of claim 1, wherein rotating the intravascular device includes rotating the intravascular device with an electric motor.

9. The method of claim 1, further including penetrating an intima of the vascular wall at a first location proximal to the occlusion in the vascular lumen and dissecting a layer of the wall.

10. The method of claim 1, further including penetrating the intima of the vascular wall at a second location distal to the occlusion in the vascular lumen.

11. The method of claim 1, further comprising positioning the tip in the vascular wall between an adventitia of the vascular wall and an intima of the vascular wall.

12. The method of claim 1, further comprising positioning the tip in the vascular wall between an adventitia of the vascular wall and the occlusion in the vascular lumen.

13. The method of claim 1, wherein the channel extends between the proximal segment and the distal segment.

14. The method of claim 1, wherein the tip has a flat distal face.

15. A method of treating a blood vessel with an intravascular device, the blood vessel having a vascular wall defining a vascular lumen containing an occlusion therein, the occlusion being disposed between a proximal segment of the vascular lumen and a distal segment of the vascular lumen, the method comprising:
    inserting an intravascular device into the vascular lumen, the intravascular device having a radiopaque marker, the intravascular device including a shaft defining a longitudinal axis and a tip located at a distal end of the shaft, wherein an outer diameter of the tip is greater than a diameter of the distal end of the shaft, a proximal portion of the tip tapering towards the shaft, the tip having a flat distal face, and wherein the intravascular device defines a device lumen;
    advancing the tip between the occlusion and an adventitia of the vascular wall;
    rotating the intravascular device to produce relative motion at an interface between the tip and surrounding tissue;
    advancing the tip between the adventitia and an intima of the vascular wall to a location distal of the occlusion;
    advancing the tip into the distal segment of the vascular lumen from the location distal of the occlusion;
    positioning a guidewire through the device lumen and into the vascular lumen beyond the occlusion; and
    withdrawing the intravascular device over the guidewire.

16. The method of claim 15, wherein receiving visual feedback confirming the rotation of the intravascular device includes:
    determining a first appearance of the radiopaque marker;
    determining a second appearance of the radiopaque marker; and
    alternating the radiopaque marker between the first appearance and the second appearance.

17. The method of claim 16, wherein the first appearance of the radiopaque marker includes a face having a width and a length, and the second appearance of the radiopaque marker includes an edge having the length and a thickness.

18. The method of claim 17, wherein the thickness is smaller than the length and the width.

19. The method of claim 17, wherein an area of the face is greater than an area of the edge.

20. The method of claim 15, further including positioning the tip in the vascular wall.

21. The method of claim 20, wherein positioning the tip in the vascular wall includes positioning the tip between the adventitia of the vascular wall and the intima of the vascular wall.

22. The method of claim 20, wherein positioning the tip in the vascular wall includes positioning the tip between the adventitia of the vascular wall and the occlusion in the vascular lumen.

23. The method of claim 15, further including advancing the intravascular device to establish a channel in the vascular wall extending longitudinally across the occlusion.

24. The method of claim 23, wherein the channel extends between the proximal segment and the distal segment.

25. The method of claim 15, wherein the intravascular device is rotated at least a plurality of revolutions.

26. The method of claim 25, wherein the intravascular device is rotated at a rotational speed between about 50 revolutions per minute and about 150 revolutions per minute.

27. A method of treating a blood vessel with an intravascular device, the blood vessel having a vascular wall defining a vascular lumen containing an occlusion therein, the occlusion being disposed between a proximal segment of the vascular lumen and a distal segment of the vascular lumen, the method comprising:
    positioning the intravascular device proximate the occlusion, the intravascular device including a shaft defining a longitudinal axis and a tip located at a distal end of the shaft, wherein an outer diameter of the tip is greater than a diameter of the distal end of the shaft, a proximal portion of the tip transitioning toward the diameter of the shaft, the intravascular device including a handle assembly disposed about the shaft, the handle assembly having a first portion and a second portion, and wherein the intravascular device defines a device lumen;
    rotating the first portion of the handle assembly relative to the second portion thus causing the handle assembly to grip the shaft at a first location along the longitudinal axis and cause rotation of the tip;
    advancing the tip of the intravascular device within the vascular wall to a location within the vascular wall distal of the occlusion to establish a channel in the vascular wall extending longitudinally across the occlusion;
    advancing the tip into the distal segment of the vascular lumen from the location within the vascular wall distal of the occlusion;
    positioning a guidewire through the device lumen and into the vascular lumen beyond the occlusion; and
    withdrawing the intravascular device over the guidewire.

28. The method of claim 27, wherein the handle assembly further includes at least one grip sleeve.

29. The method of claim 28, wherein the at least one grip sleeve is a plurality of grip sleeves.

30. The method of claim 28, wherein the at least one grip sleeve is within the handle body.

31. The method of claim 27, wherein the handle assembly is located over a proximal portion of a shaft of the intravascular device.

32. The method of claim 27, wherein the channel extends between the proximal segment and the distal segment.

33. The method of claim 27, wherein the tip has a flat distal face.

34. The method of claim 33, wherein the flat distal face includes a central aperture.

35. The method of claim 27, wherein the tip is rotated at least a plurality of revolutions.

36. The method of claim 35, wherein the tip is rotated at a rotational speed between about 50 revolutions per minute and about 150 revolutions per minute.

37. A method of treating a blood vessel with an intravascular device, the blood vessel having a vascular wall defining a vascular lumen containing an occlusion therein, the occlusion being disposed between a proximal segment of the vascular lumen and a distal segment of the vascular lumen, the method comprising:
    inserting an intravascular device having a shaft with a longitudinal axis into the vascular lumen, wherein a tip is fixed to a distal end of the shaft, wherein an outer diameter of the tip is greater than a diameter of the distal end of the shaft, and a handle assembly is attached to a proximal end of the shaft, and wherein the intravascular device defines a device lumen;
    positioning the tip near the occlusion;
    advancing the tip between the occlusion and an adventitia of the vascular wall;
        rotating the handle assembly to cause rotation of the tip about the longitudinal axis between the occlusion and the adventitia while advancing the tip to a location distal of the occlusion;
        wherein rotating the handle assembly and advancing the tip occur simultaneously, the intravascular device being rotated at least a plurality of revolutions at a rotational speed between about 50 revolutions per minute and about 150 revolutions per minute;
        passing the tip into the distal segment of the vascular lumen from the location distal of the occlusion;
        positioning a guidewire through the device lumen and into the vascular lumen beyond the occlusion; and
        withdrawing the intravascular device over the guidewire.

38. The method of claim 37, further including stopping rotating and advancing the tip when the tip of the intravascular device is advanced beyond the occlusion in the vascular lumen.

39. The method of claim 37, further including penetrating an intima of the vascular wall at a first location proximal to the occlusion in the vascular lumen and dissecting a layer of the wall.

40. The method of claim 37, wherein the shaft includes a coil having a plurality of filars wound in a helical shape, the coil extending from the distal end of the shaft to the proximal end of the shaft, the intravascular device further including a hub fixed to the proximal end of the shaft and a sleeve extending from a distal end of the shaft and covering a portion of the coil.

41. The method of claim 40, wherein the intravascular device further includes a sheath having a proximal end and a distal end, and covering a portion of the coil and a portion of the sleeve, the proximal end of the sheath located proximal to the proximal end of the sleeve, and the distal end of the sheath located proximal to the distal end of the sleeve.

42. The method of claim 40, wherein the intravascular device further includes a tube body having a proximal end and a distal end, and covering a portion of the coil and a portion of the sleeve, the distal end of the tube body extending beyond the proximal end of the sleeve, and the proximal end of the tube body is fixed to the hub.

43. The method of claim 37, wherein the handle assembly is slidably positioned about the intravascular device.

44. The method of claim 37, where the handle assembly is located about the intravascular device, the handle assembly comprising:
    a handle body threadedly connected to a handle cap, the handle cap being configured to rotate relative to the handle body; and
    at least one member configured to grip a shaft of the intravascular device in response to a rotation of the handle cap relative to the handle body.

45. The method of claim 37, wherein a channel extends between the proximal segment and the distal segment.

46. The method of claim 37, wherein the tip has a proximal portion that tapers towards the shaft.

47. The method of claim 37, wherein the tip has a flat distal face.

* * * * *